(12) United States Patent
Iqbal et al.

(10) Patent No.: US 9,737,587 B2
(45) Date of Patent: Aug. 22, 2017

(54) TREATMENT OF AUTISM SPECTRUM DISORDERS WITH CILIARY NEUROTROPHIC FACTOR PEPTIDE MIMETIC

(71) Applicant: The Research Foundation for Mental Hygiene, Inc., Menands, NY (US)

(72) Inventors: Khalid Iqbal, Staten Island, NY (US); Inge Grundke-Iqbal, Staten Island, NY (US)

(73) Assignee: The Research Foundation for Mental Hygiene, Inc., Menands, NY (US)

( * ) Notice: Subject to any disclaimer, the term of this patent is extended or adjusted under 35 U.S.C. 154(b) by 20 days.

(21) Appl. No.: 14/950,569

(22) Filed: Nov. 24, 2015

(65) Prior Publication Data
US 2016/0143993 A1    May 26, 2016

Related U.S. Application Data

(60) Provisional application No. 62/083,570, filed on Nov. 24, 2014.

(51) Int. Cl.
*A61K 38/00* (2006.01)
*A01N 37/18* (2006.01)
*A61K 38/18* (2006.01)

(52) U.S. Cl.
CPC .................................. *A61K 38/185* (2013.01)

(58) Field of Classification Search
None
See application file for complete search history.

(56) References Cited

U.S. PATENT DOCUMENTS 8,338,378 B2 * 12/2012 Mossler ............... C07K 14/475
514/16.5
8,592,374 B2 * 11/2013 Mosler ................. C07K 5/1008
514/16.5
9,327,011 B2 * 5/2016 Iqbal ...................... A61K 38/08

\* cited by examiner

*Primary Examiner* — Olga N Chernyshev
(74) *Attorney, Agent, or Firm* — Bond Schoeneck and King PLLC; David Nocilly

(57) ABSTRACT

A method of treating autism spectrum disorders using a therapeutic amount of a synthetic amino acid sequence corresponding to a portion of human ciliary neurotrophic factor (CNTF). In particular, the synthetic amino acid sequence is VGDGGLFEKKL (SEQ ID NO: 1), referred to as Peptide 6. Peptide 6 was tested and shown to exert a neuroprotective effect by modulating CNTF/JAK/STAT pathway and LIF signaling and enhancing brain derived neurotrophic factor (BDNF) expression.

6 Claims, 30 Drawing Sheets

Figure 1A:
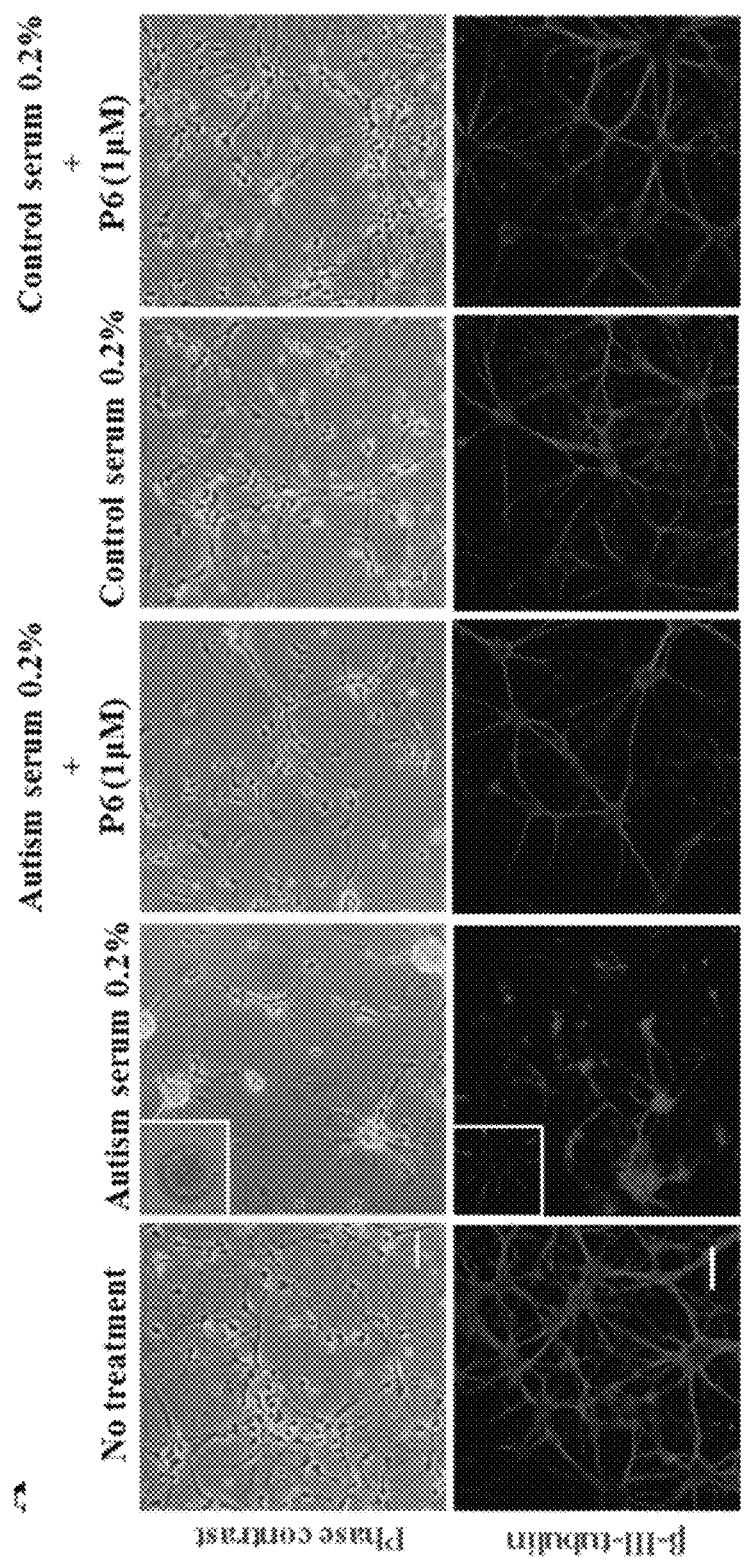

TREATMENT OF AUTISM SPECTRUM DISORDERS WITH CILIARY NEUROTROPHIC FACTOR PEPTIDE MIMETIC

BACKGROUND OF THE INVENTION

1. Field of the Invention

The present invention relates to the treatment of autism and, more specifically, the use of a ciliary neurotrophic factor peptide mimetic to address autism disorders.

2. Description of the Related Art

Autism and autism spectrum disorders (ASDs) are neurodevelopmental disorders of as yet unknown etiology characterized clinically by a behavioral phenotype comprising of impaired social interaction, absence or delay in language, and repetitive, stereotyped purposeless behavior. The onset of symptoms usually occurs after 3 years of life. The prevalence of autism has increased dramatically over the last decade with most recent Center for Disease Control and Prevention (CDC) estimates suggesting that ASDs affect 1 in 88 children in U.S. with a five-fold higher occurrence in boys as compared to girls. Even though the exact etiology of autism is as yet not precisely elucidated, existing scientific literature suggests a multifactorial etiopathogenesis encompassing genetic, environmental, and immunological factors, neurotrophic dysregulation, and an increased susceptibility to oxidative stress.

A consistent phenomenon reported in scientific literature on autism cases is an accelerated brain growth during early development followed by slowed brain growth and decreased neuronal number and size and less dendritic branching in various brain regions such as cerebellum, hippocampus, and amygdala. These findings point towards an abnormality in regulatory mechanisms that govern growth and differentiation of central nervous system leading to an imbalance in neuronal and synaptic formation and pruning. One of the most prominent factors in neurogenesis, neuronal proliferation, differentiation, and pruning in normal brain development is the microenvironment provided by various neurotrophic factors. A dysregulation of neurotrophic factors can be a major cause of abnormalities in neurogenesis, neuronal migration and differentiation, synaptic connectivity and maturation, and neuronal and synaptic pruning leading to deficits in social behavior and cognition observed in autism.

Alterations in the levels of neurotrophic factors in the brain, cerebrospinal fluid (CSF), and blood of individuals with autism have been reported extensively. A main cause of dysregulation of neurotrophic factors in autism might be oxidative stress during prenatal and early development which is a widely implicated in the pathogenesis of autism. For example, increased oxidative stress has been shown to block ciliary neurotrophic factor (CNTF) activity in neurons which is essential for neuronal survival and maintenance. On a similar note, serum levels of brain-derived neurotrophic factor (BDNF) have been linked to oxidative stress in ASDs. Previously, cerebrolysin, a peptidergic neurotrophic preparation which has been shown to protect chicken cortical neurons from neurodegeneration in an iron-induced oxidative stress model and to enhance dentate gyms neurogenesis and associated memory in normal adult rats was found to improve expressive and receptive speech and fine motor performance in 17 out of 19 children with autism. Targeting the neurotrophic abnormalities in autism can, thus, serve as potential therapeutic approach.

The therapeutic usage of neurotrophic factor such as BDNF and CNTF has been limited primarily because full-length neurotrophic factor molecules poorly reach the central nervous system after peripheral administration and have short plasma half-lives. Besides, recombinant CNTF was shown to cause anorexia, skeletal muscle loss, hyperalgesia, severe cramps, and muscle pain in human clinical trials.

BRIEF SUMMARY OF THE INVENTION

The present invention comprises the use of Peptide 6 (P6) to treat autism. Peptide 6 is an 11-mer peptide derived from ciliary neurotrophic factor (CNTF) and exerts a beneficial effect on neurogenesis, neuronal and synaptic plasticity, and cognition via inhibition of LIF signaling pathway and elevation of BDNF level by increasing its transcription. To establish the efficacy of the use of Peptide 6 to treat autism, an example was performed where: (i) sera from children with autism were used to cause neurodegeneration and increased oxidative stress in embryonic day 18 mouse primary neuronal cultures; (ii) the intracerebroventricular injection of the autistic sera within hours after birth was used to produce characteristic autistic behavioral phenotype in young rats; and (iii) pre-treatment with P6 was found to be neuroprotective to autistic sera-induced changes both in mouse primary neuronal cultures and in vivo in rats.

BRIEF DESCRIPTION OF THE SEVERAL VIEWS OF THE DRAWING(S)

The present invention will be more fully understood and appreciated by reading the following Detailed Description in conjunction with the accompanying drawings, in which:

FIG. 1A is a series of representative images of phase contrast microscopy and β-III-tubulin (mature neuronal marker) staining of DIV7 primary cultured cortical neurons treated with 0.2% sera from autistic or control children with or without 1 μM P6 for 72 hours showing the effect of autism and control sera treatment with or without P6 on neuronal morphology. Data is based on evaluation of the effect of 22 pairs of autism/control sera in 3 independent set of experiments. Autism sera markedly reduced the length of the neurites and the number of cells and showed increased number of cell spheres and P6 could rescue these changes.

Figure 1B:
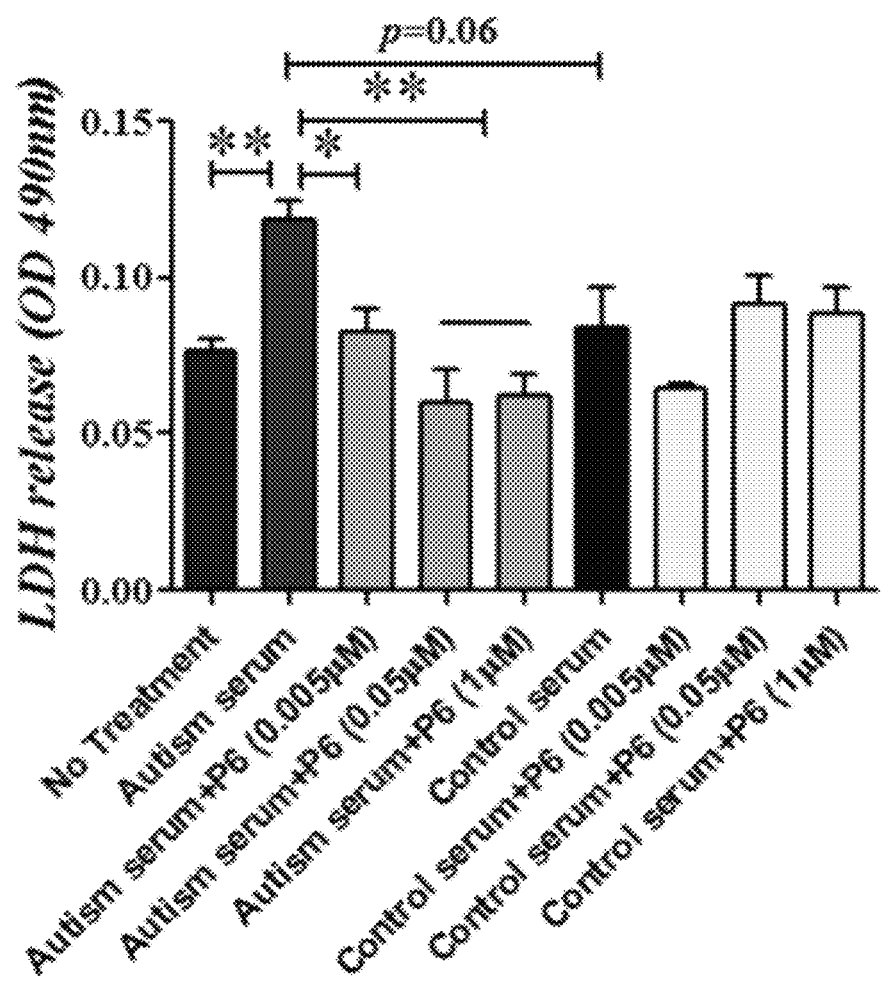
Figure 1C:
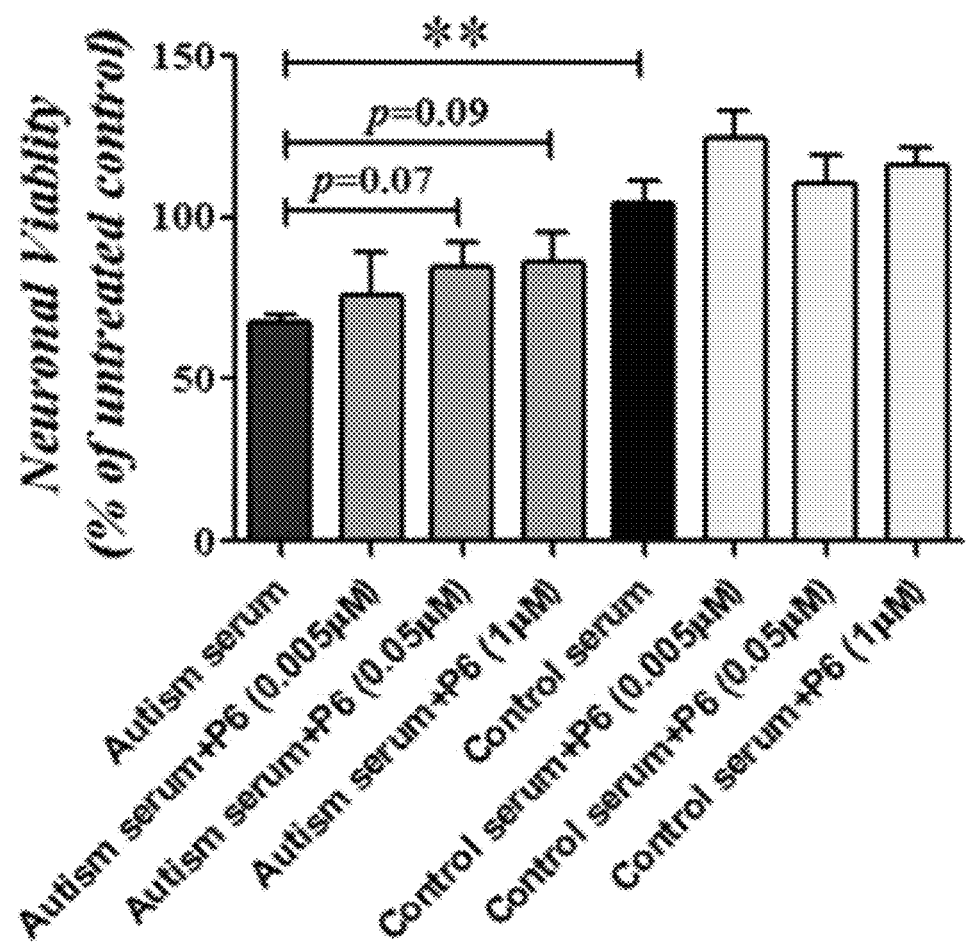

FIGS. 1B and 1C are graphs of the quantification of LDH cytotoxicity assay for evaluation of cell death (LDH release) and neuronal viability in DIV7 primary cultured cortical neurons treated with 0.2% sera from autistic or control children with or without 1 μM P6 for 72 hours. Data are shown as mean+S.E.M. based on the effect of 3 pairs of autism/control sera in 3 independent sets of experiments.

Figure 1D:
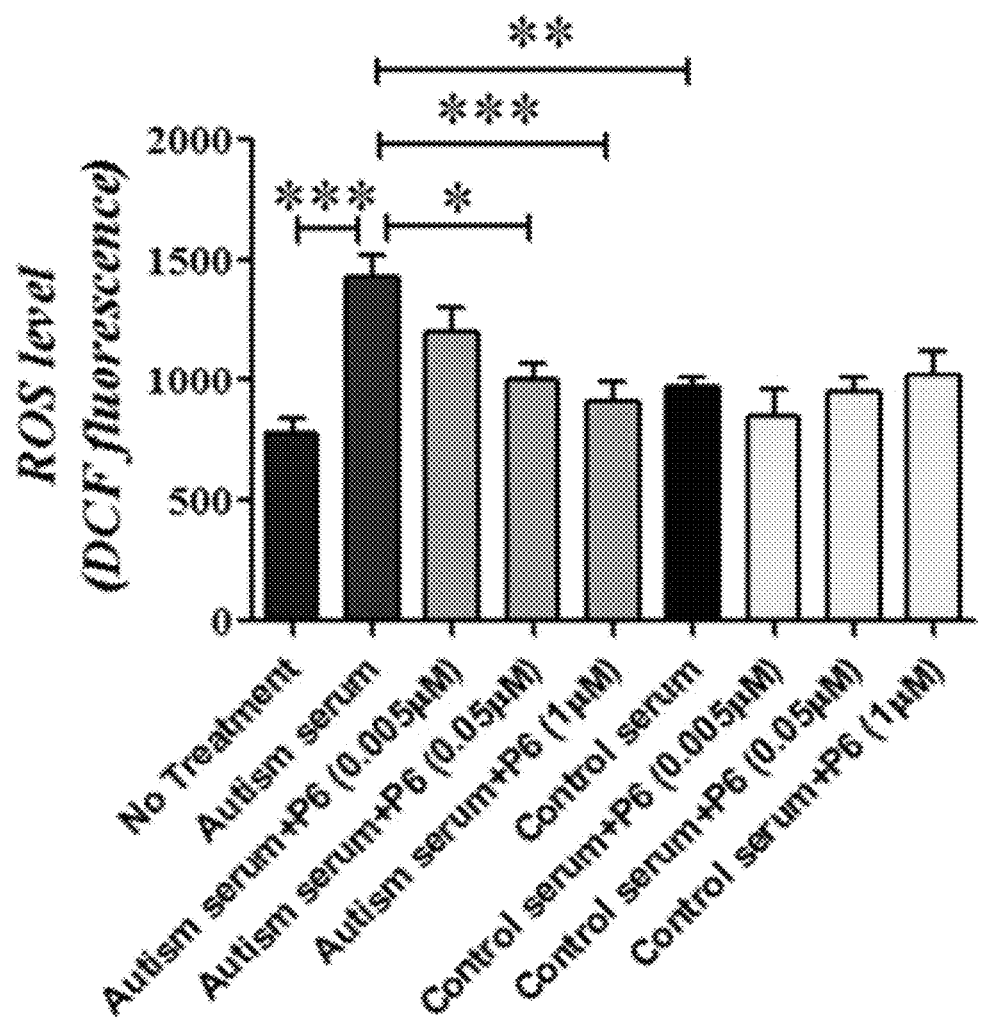
Figure 1E:
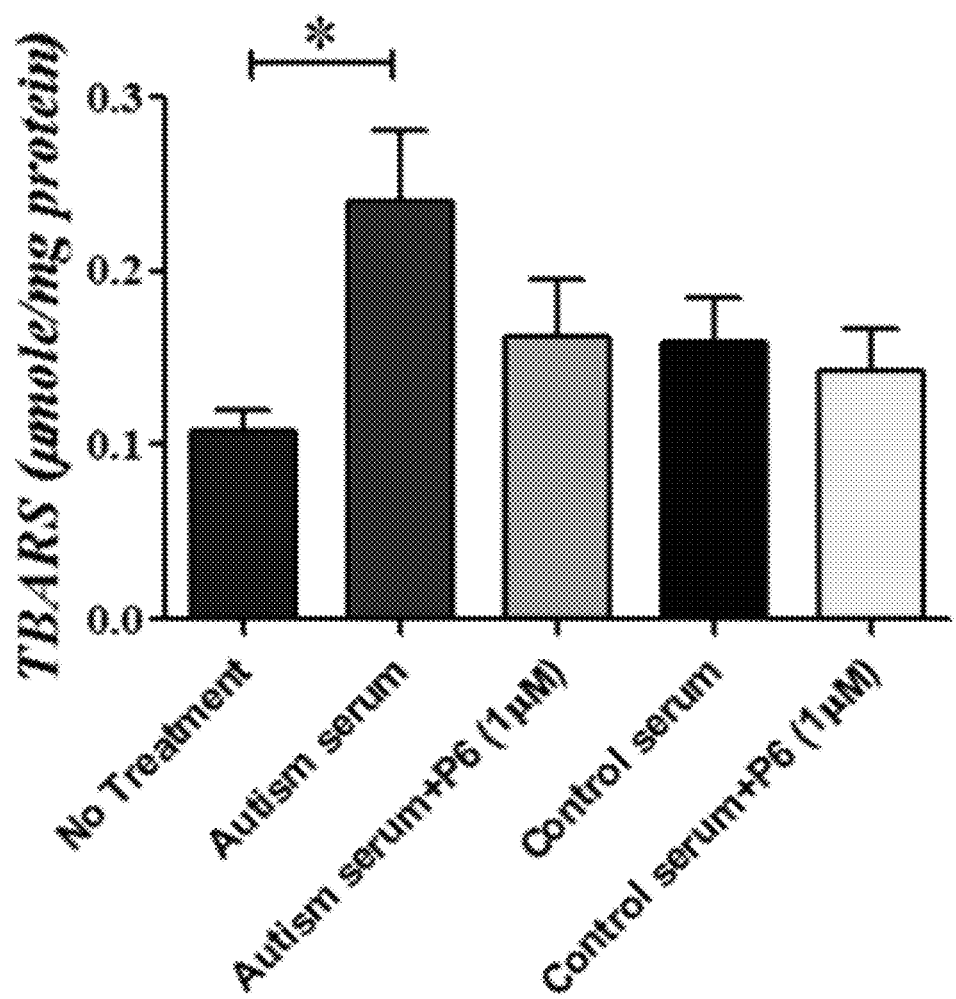

FIGS. 1D and 1E are graphs showing oxidative stress data from a DCF-DA assay for free radical production and TBARS assay for lipid peroxidation 3 days after treatment (DIV7) with sera from autistic or control children) with or without P6 pre-treatment (0.005 μM, 0.05 μM, and 1 μM). Data are shown as mean+S.E.M. based on two independent sets of experiments evaluating 3 pairs of autism/control sera. $*p<0.05$, $p<0.01$, and $*p<0.001$. ANOVA with Bonferroni's post-hoc test and/or Student's t-test (scale bar=100 μm).

Figure 2A:
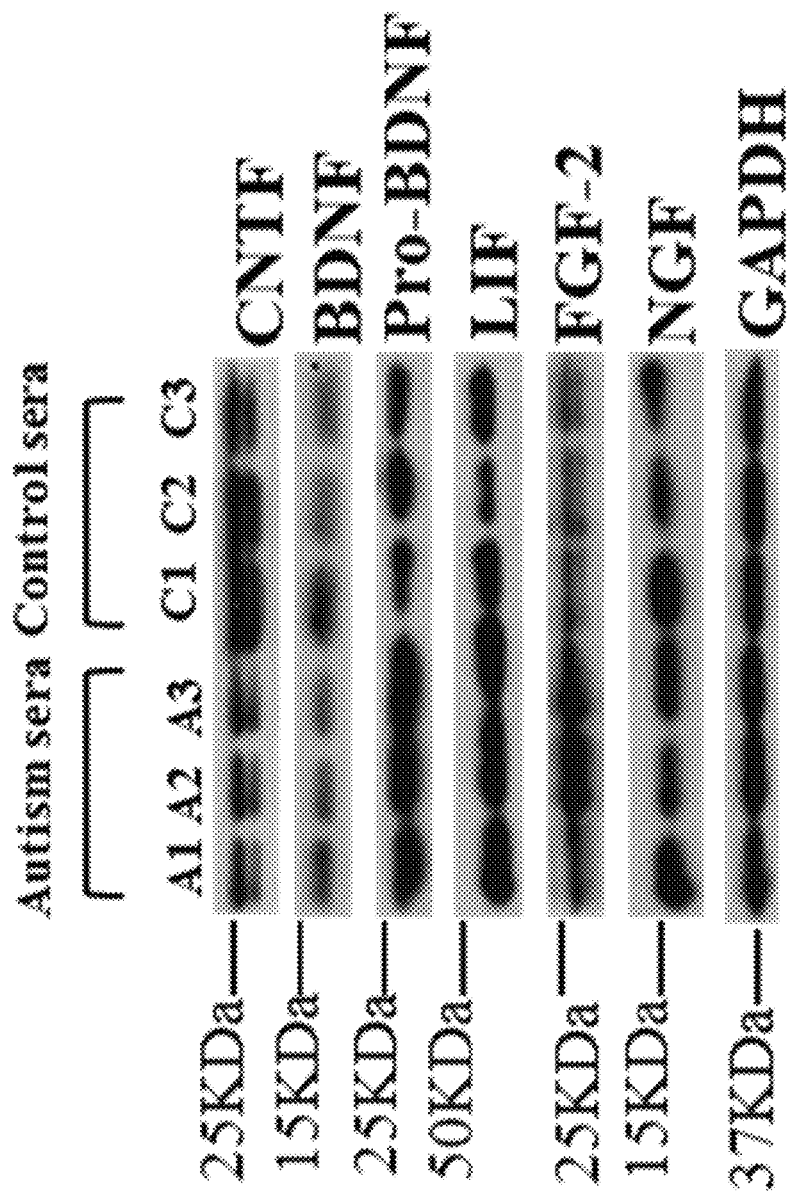
Figure 2B:
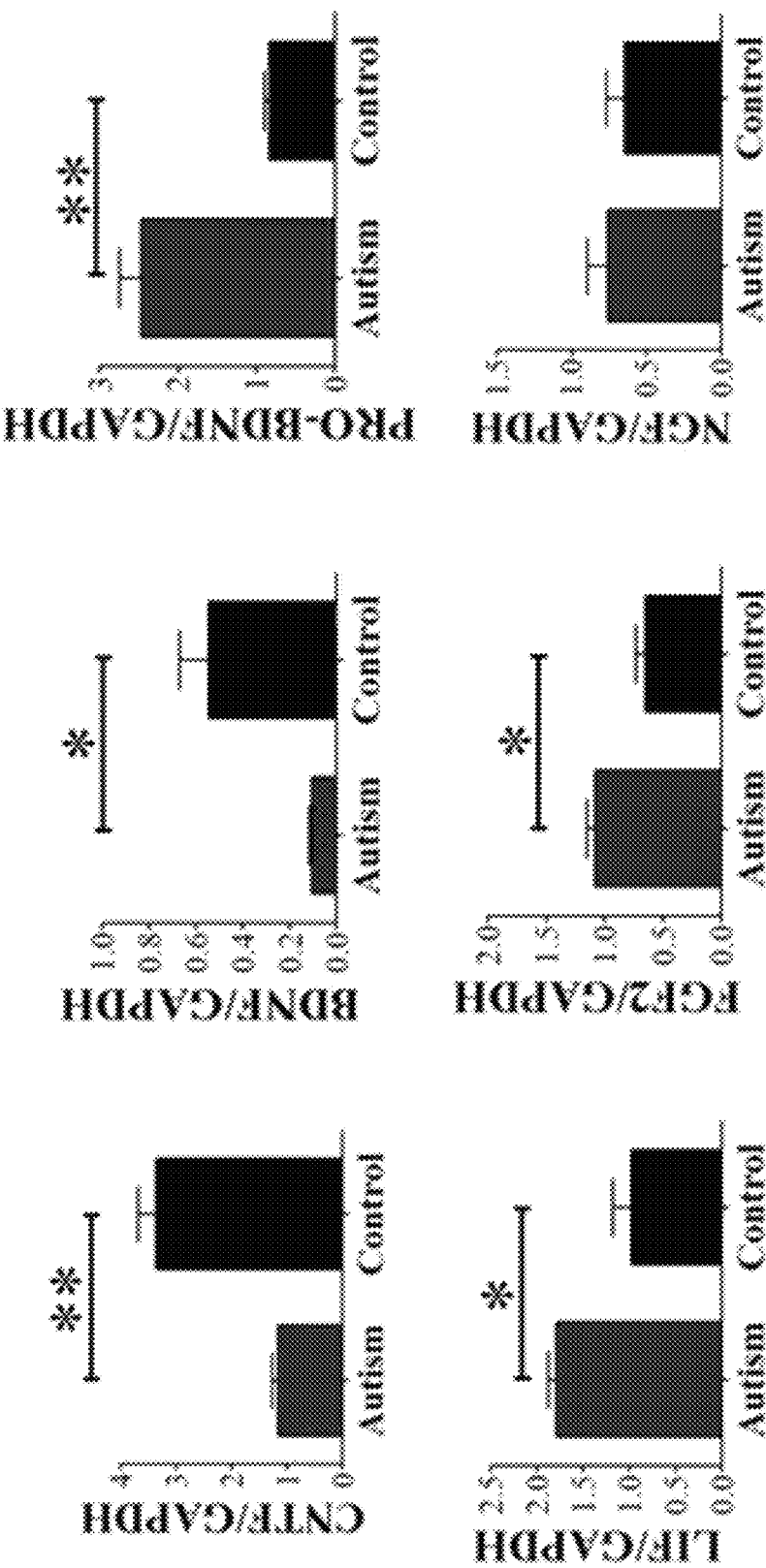

FIGS. 2A and 2B are representative images and graphical quantifications of Western blots for evaluation of levels of various neurotrophic factors in 3 pairs of sera from autistic and control children used in the study showing the levels of various neurotrophic factors in sera from autistic and control children. A1, A2, A3, and C1, C2, C3, represent 3 autism and 3 control cases, respectively and *p<0.05, p<0.01, and *p<0.001 (Student's t-test).

Figure 3A:
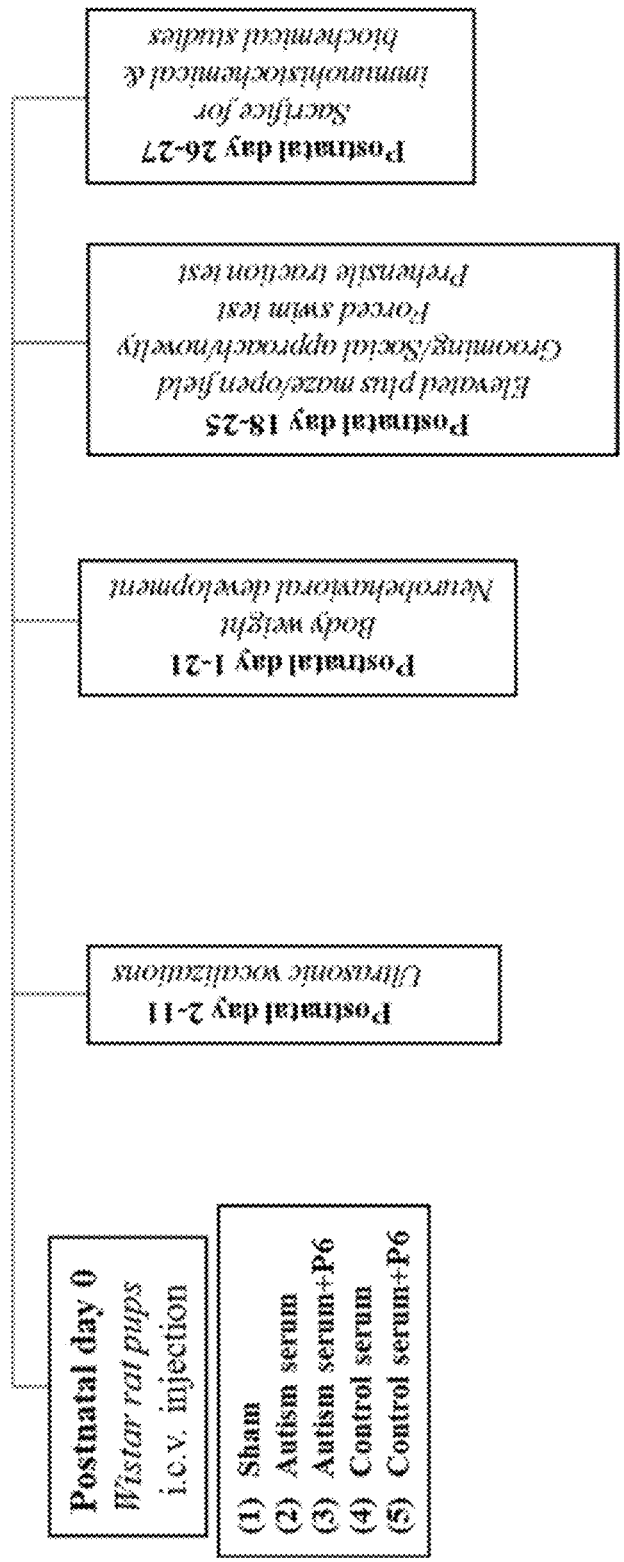

FIG. 3A is a schematic of the design of an in vivo study where newly born Wistar rat pups were injected intracerebroventricularly on postnatal day (P)0.5 with saline (sham) or ~2% (final concentration) autism or control serum with or without ~20 nM (final concentration) P6. Behavioral studies were performed from postnatal day 2 to 25 in rats and the effects of autism and control sera in the presence or absence of P6 on neurobehavioral development in rats.

Figure 3B:
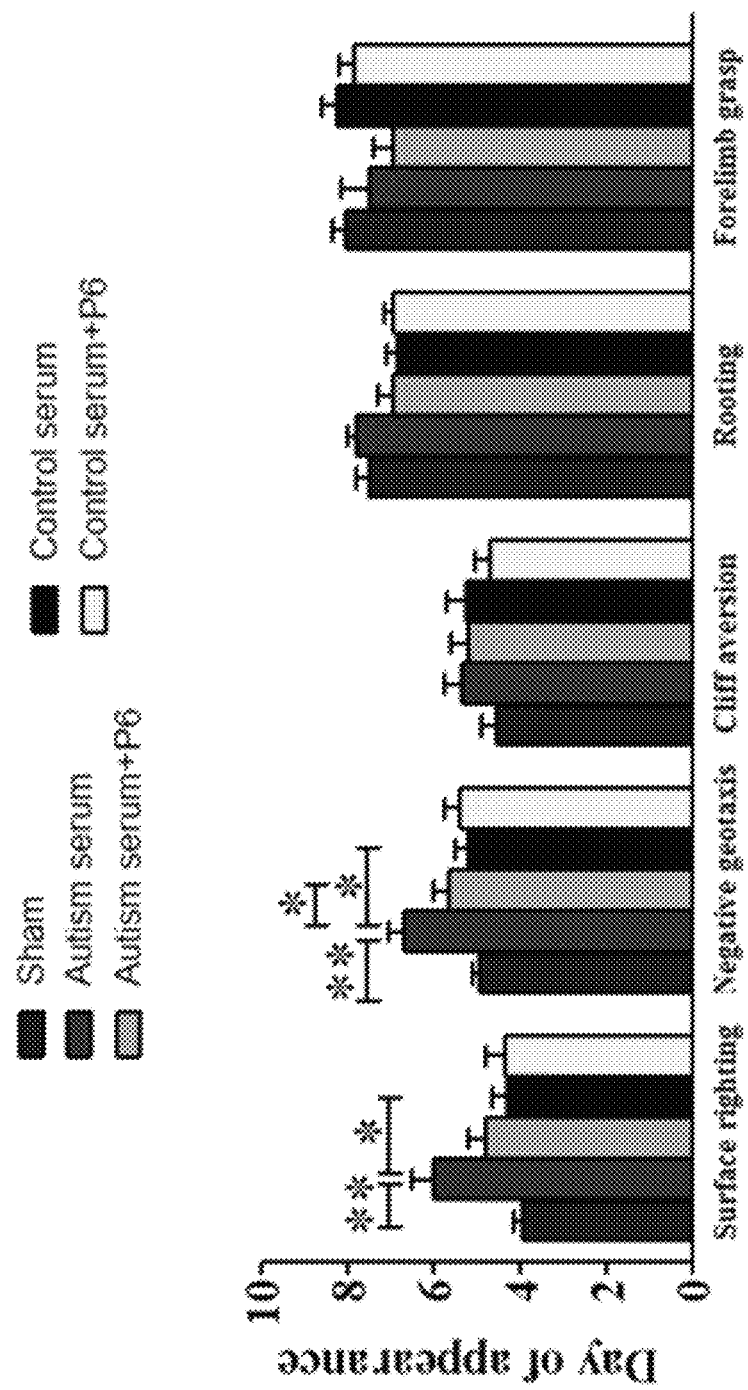
Figure 3C:
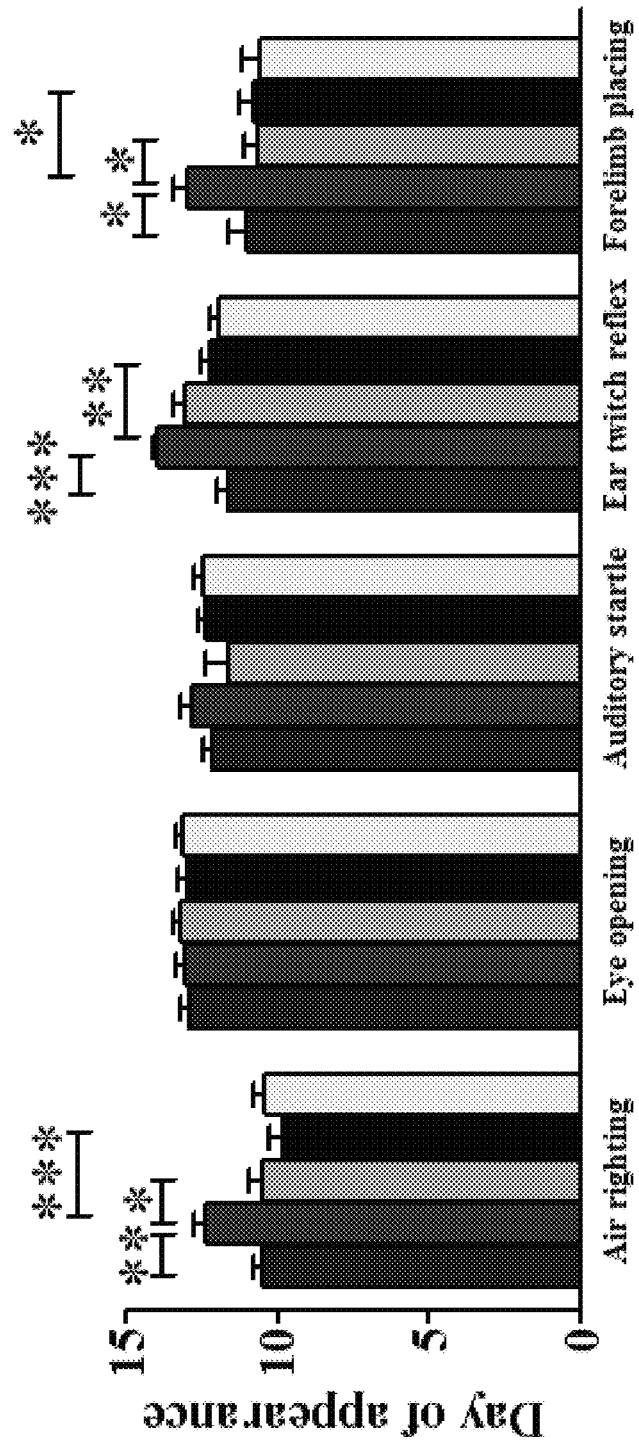

FIGS. 3B and 3C are a series of graphs of the evaluation of neurobehavioral development in Wistar rat pups from postnatal day 1-21, wherein FIG. 3B includes the day of appearance of surface righting, negative geotaxis, cliff aversion, rooting, and forelimb grasp and FIG. 3C includes air righting, eye opening, auditory startle, ear twitch reflex, and fore limb placing. Data are presented as mean+S.E.M. based on sham (n=17), autism serum (n=15-16), autism serum+P6 (n=16-17), control serum (n=15-16), and control serum+P6 (n=16-17) and *p<0.05, p<0.01, and *p<0.001 (ANOVA with Bonferroni's post-hoc test and/or Student's t-test).

Figure 4A:
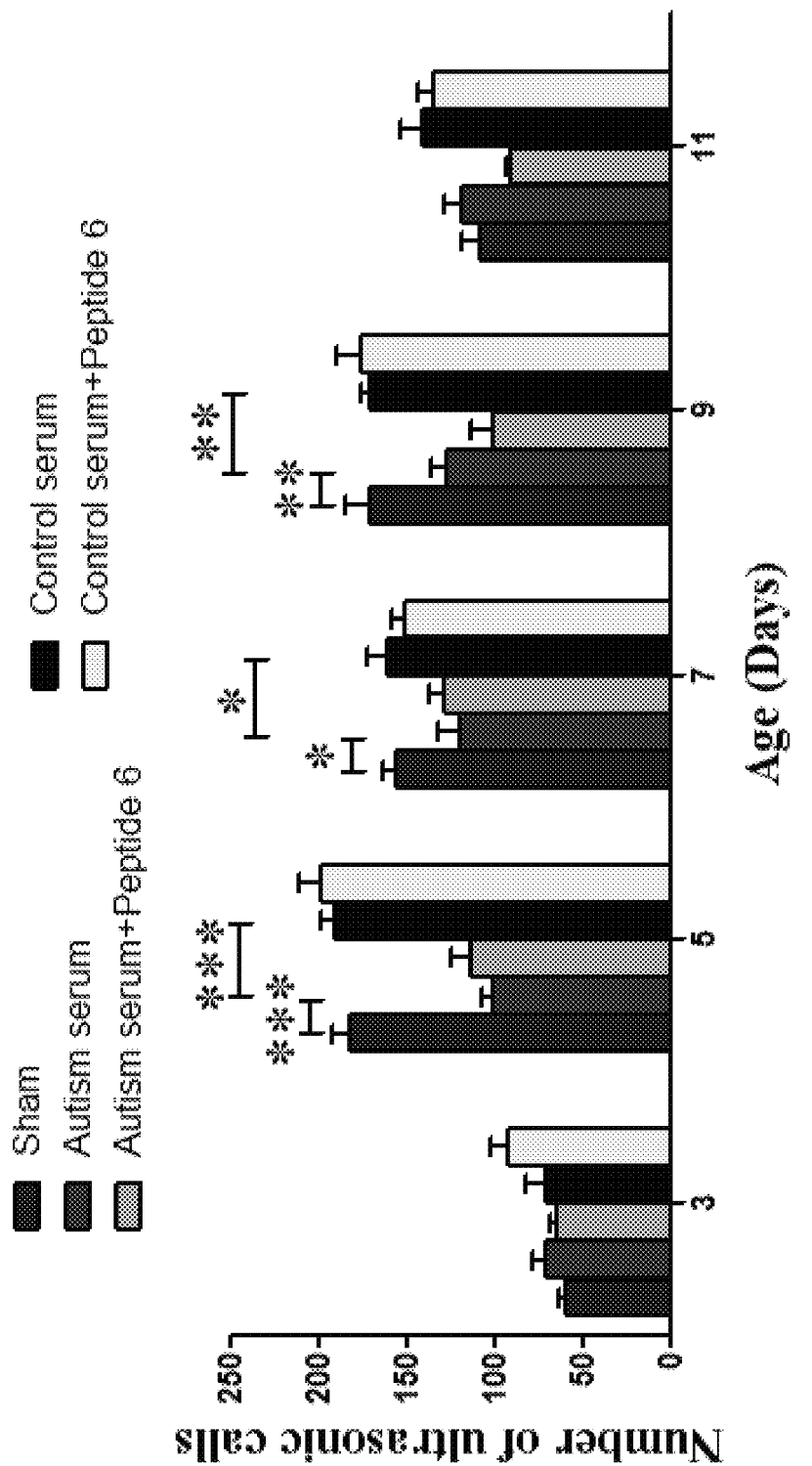
Figure 4B:
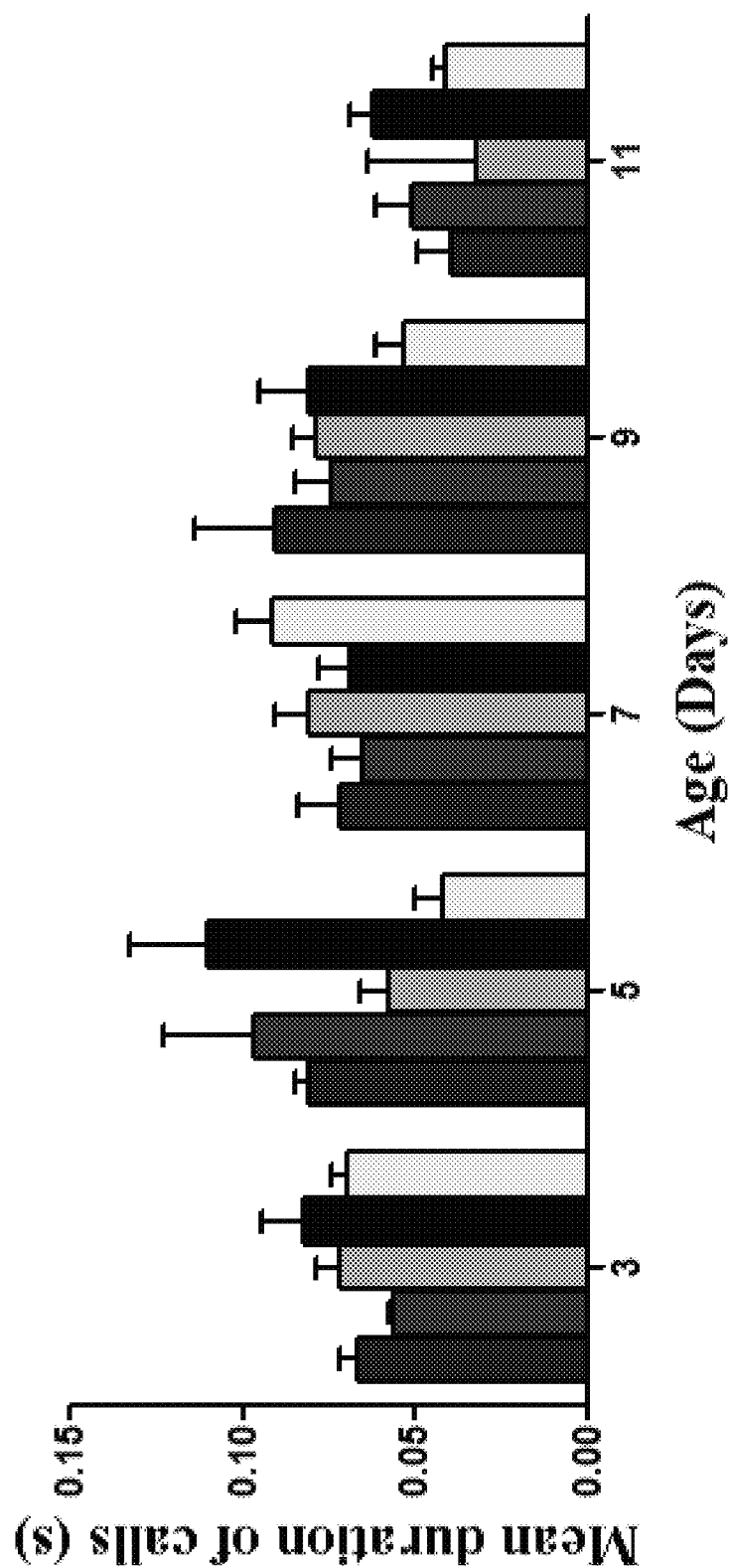

FIGS. 4A and B are a series of graphs of the effects of autism and control sera in the presence or absence of P6 on ultrasonic vocalizations (USVs) from postnatal day 2-11 in rat pups. Social communication in young Wistar rats injected intracerebroventricularly on P0.5 with sham or 2% autism or control serum with or without 20 nM P6. Social communication was evaluated by the number, FIG. 4A, and duration, FIG. 4B, of isolation induced ultrasonic calls emitted by rat pups during the 5 min test on postnatal days 3, 5, 7, 9, and 11. Data are presented as mean+S.E.M. in saline (sham) (n=15-17), autism serum (n=15-17), autism serum+P6 (n=15-17), control serum (n=15-17), and control serum+P6 (n=15-17) treated pups where *p<0.05, p<0.01, and *p<0.001 (ANOVA with Bonferroni's post-hoc test and/or Student's t-test).

Figure 5A:
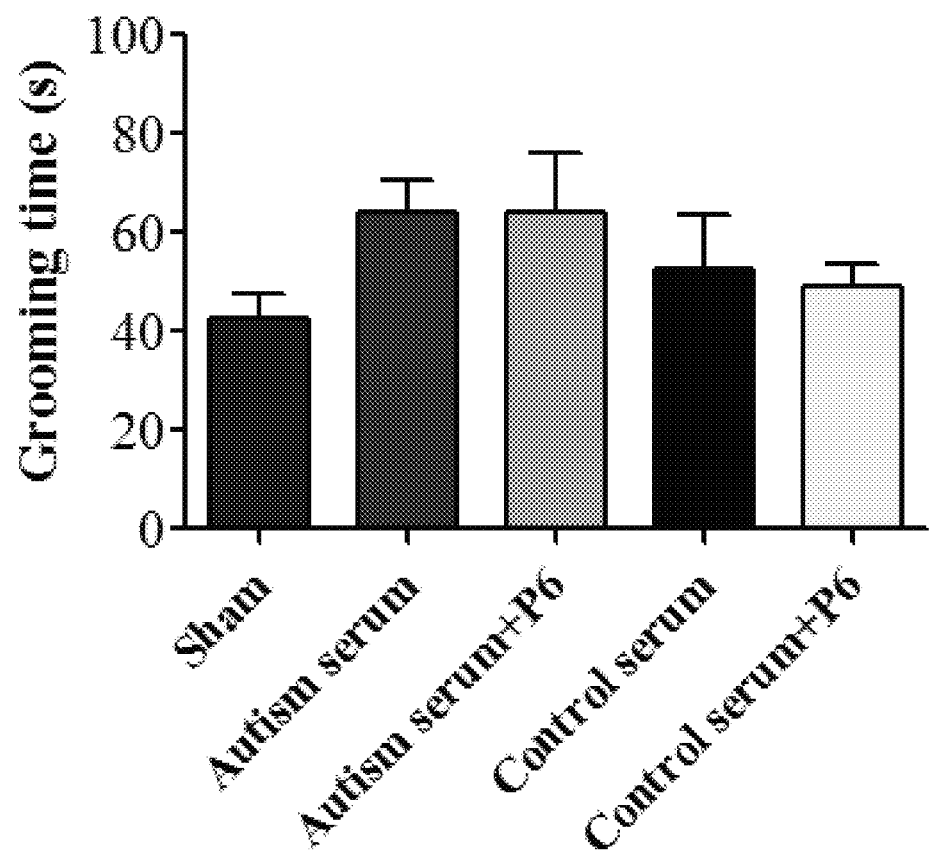
Figures 5B, 5C:
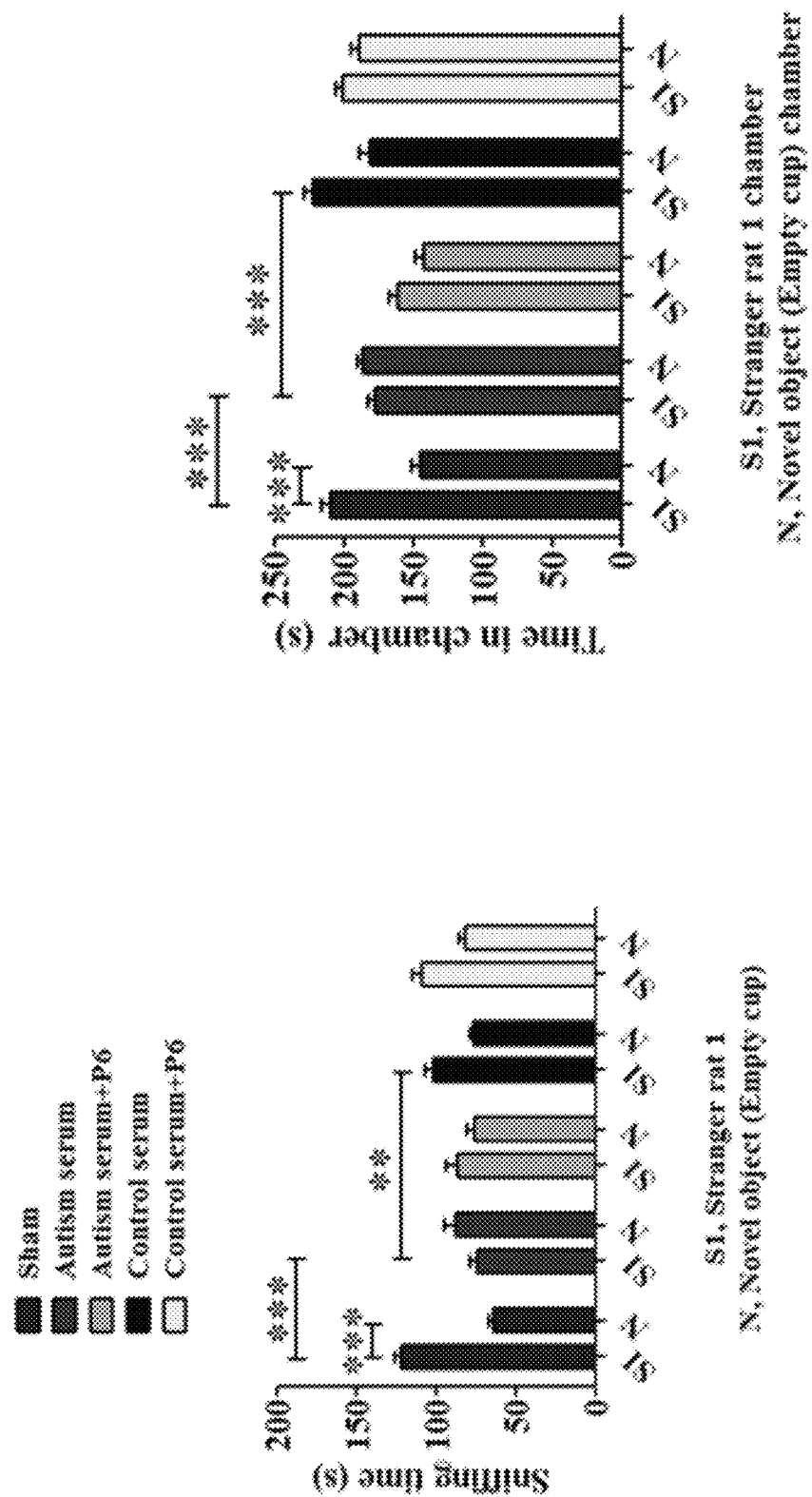
Figure 5E:
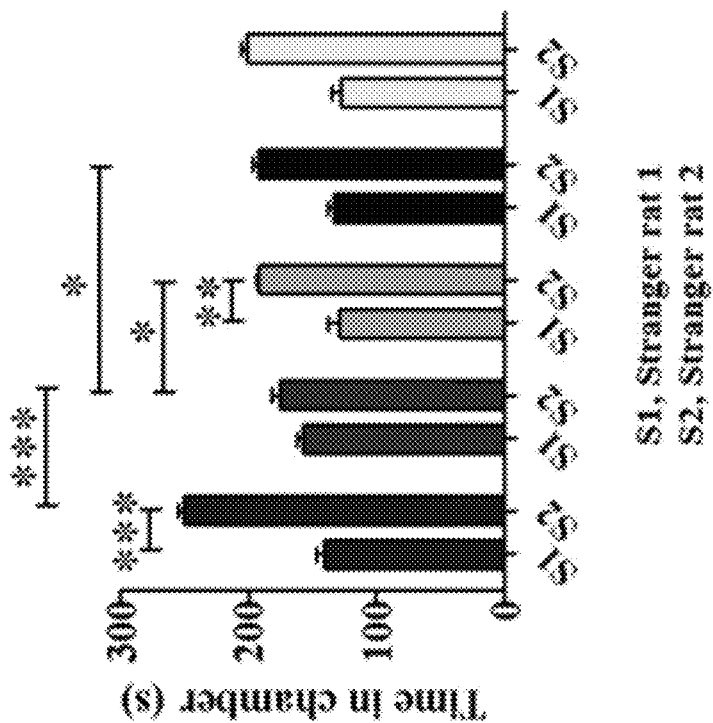
Figure 5D:
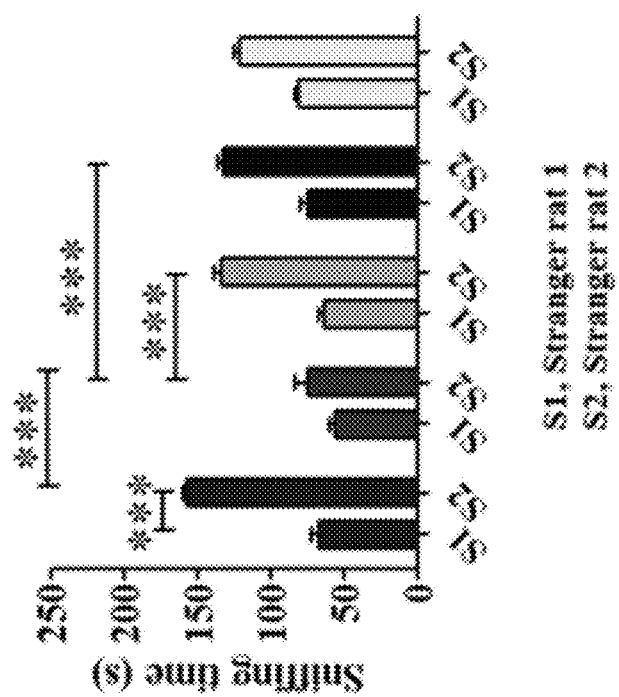

FIGS. 5A through 5E are a series of graphs of the effect of autism and control sera in the presence or absence of P6 on grooming, social approach and novelty in young Wistar rats. P0.5 rat pups were injected intracerebroventricularly with saline (sham) or 2% autism or control serum with or without 20 nM P6. FIG. 5A includes grooming time measured during the first 5 min habituation phase in the central chamber of the 3-chamber social approach/novelty task. FIG. 5B includes sniffing time and time in the chamber (stranger rat 1 versus novel object) spent in the social approach task. FIG. 5C includes sniffing time, FIG. 5D, and time in the chamber, FIG. 5E, (stranger rat 1 versus stranger rat 2) spent in the social novelty task. Data are presented as mean+S.E.M. based on sham (n=15), autism serum (n=15), autism serum+P6 (n=16), control serum (n=15), and control serum+P6 (n=16) with *p<0.05, p<0.01, and *p<0.001 (ANOVA with Bonferroni's post-hoc test and/or Student's t-test).

Figure 6A:
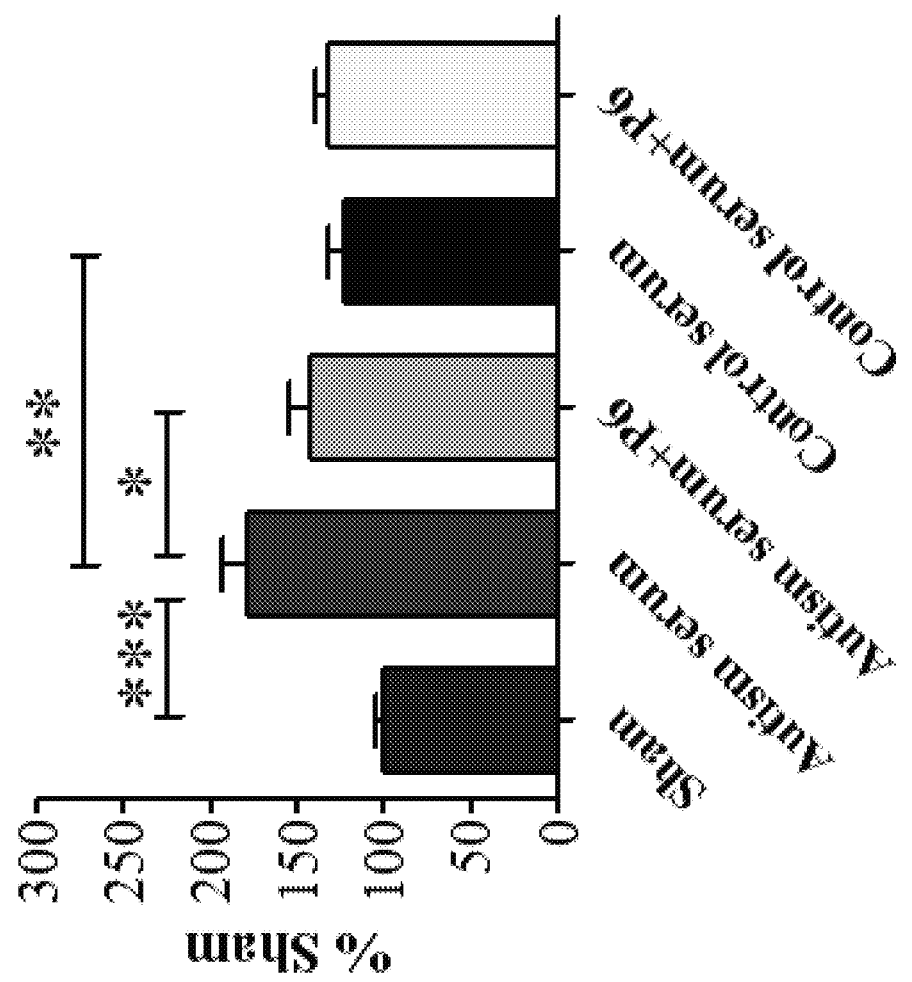
Figure 6B:
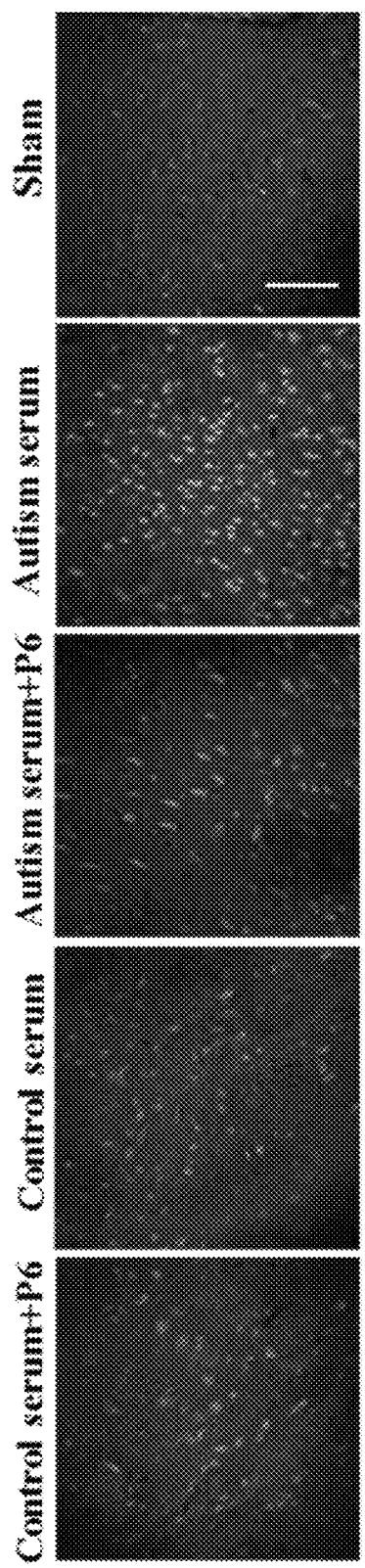
Figure 6C:
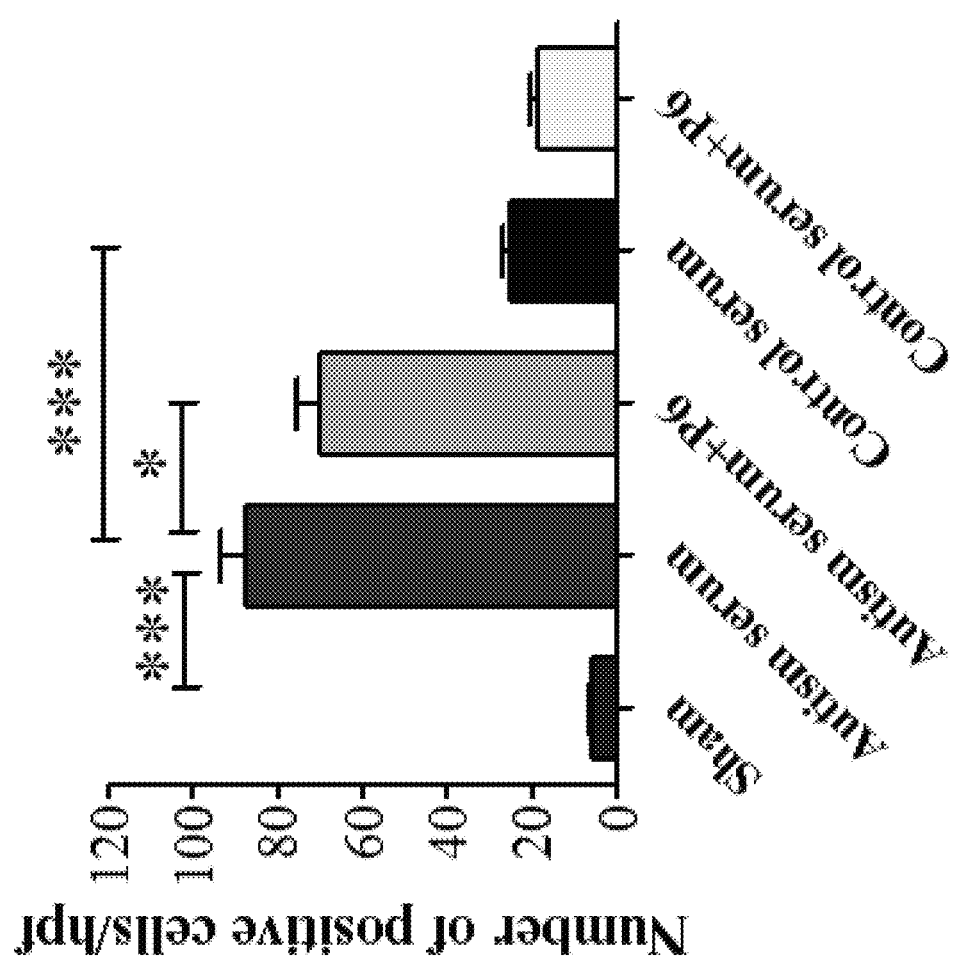
Figure 6D:
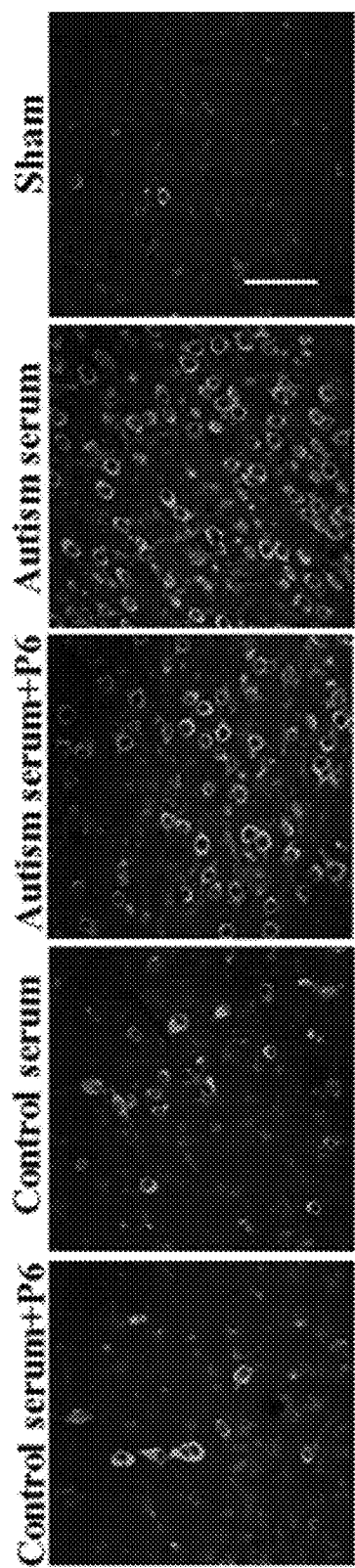
Figure 6E:
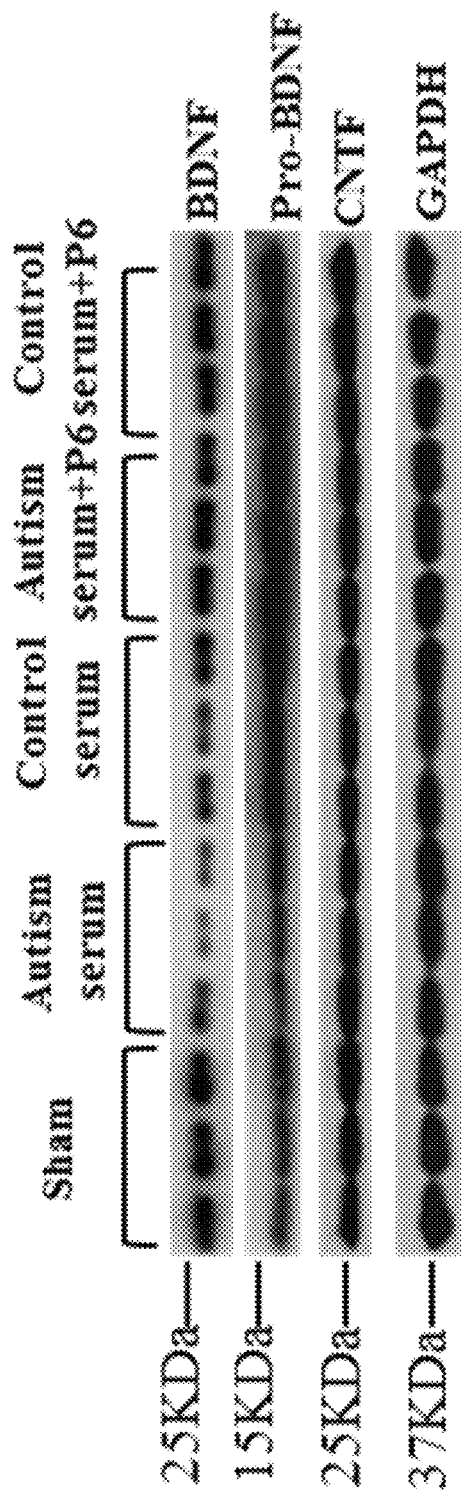
Figure 6F:
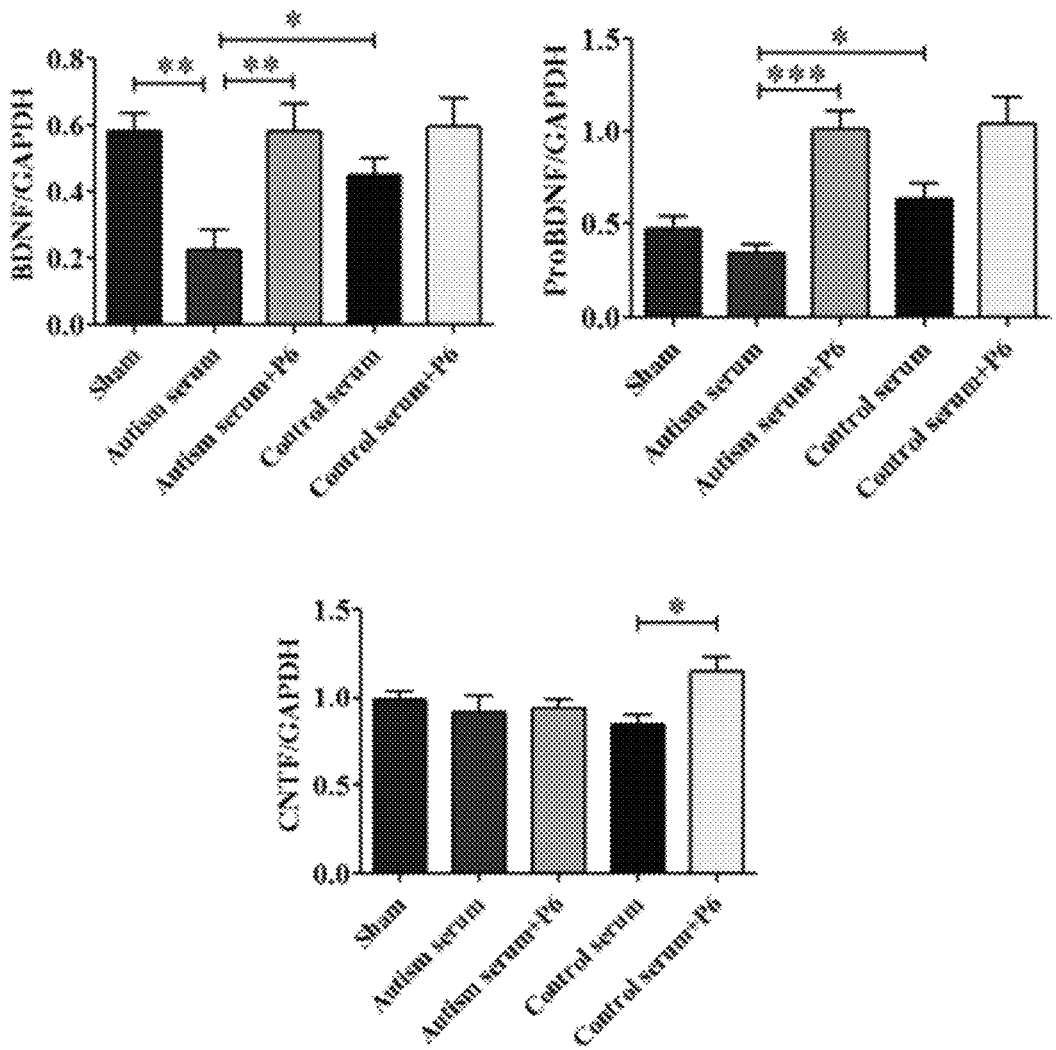

FIG. 6A through 6F are images and graphs of the effect of autism and control sera in the presence or absence of P6 on neurodegeneration, oxidative stress, and CNTF, BDNF, and pro-BDNF expression in the cerebral cortex of young Wistar rats. On day P0.5, rats were injected intracerebroventricularly with saline (sham) or 2% autism or control serum with or without 20 nM P6. On postnatal day 26-27, rats were sacrificed and their brain tissue was evaluated by quantitative immunohistochemistry and Western blots. FIG. 6A and 6B are a graph of the quantification (% sham) and representative images of Fluorojade C staining, a sensitive marker of neurodegeneration, in the cerebral cortex. Quantification is based on minimum of 6 animals/group (including 2 animals for each serum sample injected). FIGS. 6C and 6D are a graph of the quantification and representative images of 8-OHdG positive neurons, a marker of DNA damage caused by oxidative free radicals, in the cerebral cortex. Quantification is based on minimum of 6 animals/group (including 2 animals for each serum sample injected). FIGS. 6E and 6F are representative Western blots and densitometric quantification of BDNF, pro-BDNF, and CNTF expression normalized to GAPDH in the cerebral cortex of young Wistar rats. Data are presented as mean+S.E.M. based on sham (n=7), autism serum (n=7), autism serum+P6 (n=8), control serum (n=6), and control serum+P6 (n=7) with *p<0.05, p<0.01, and *p<0.001 (ANOVA with Bonferroni's post-hoc test and/or Student's t-test).

Figure 7:
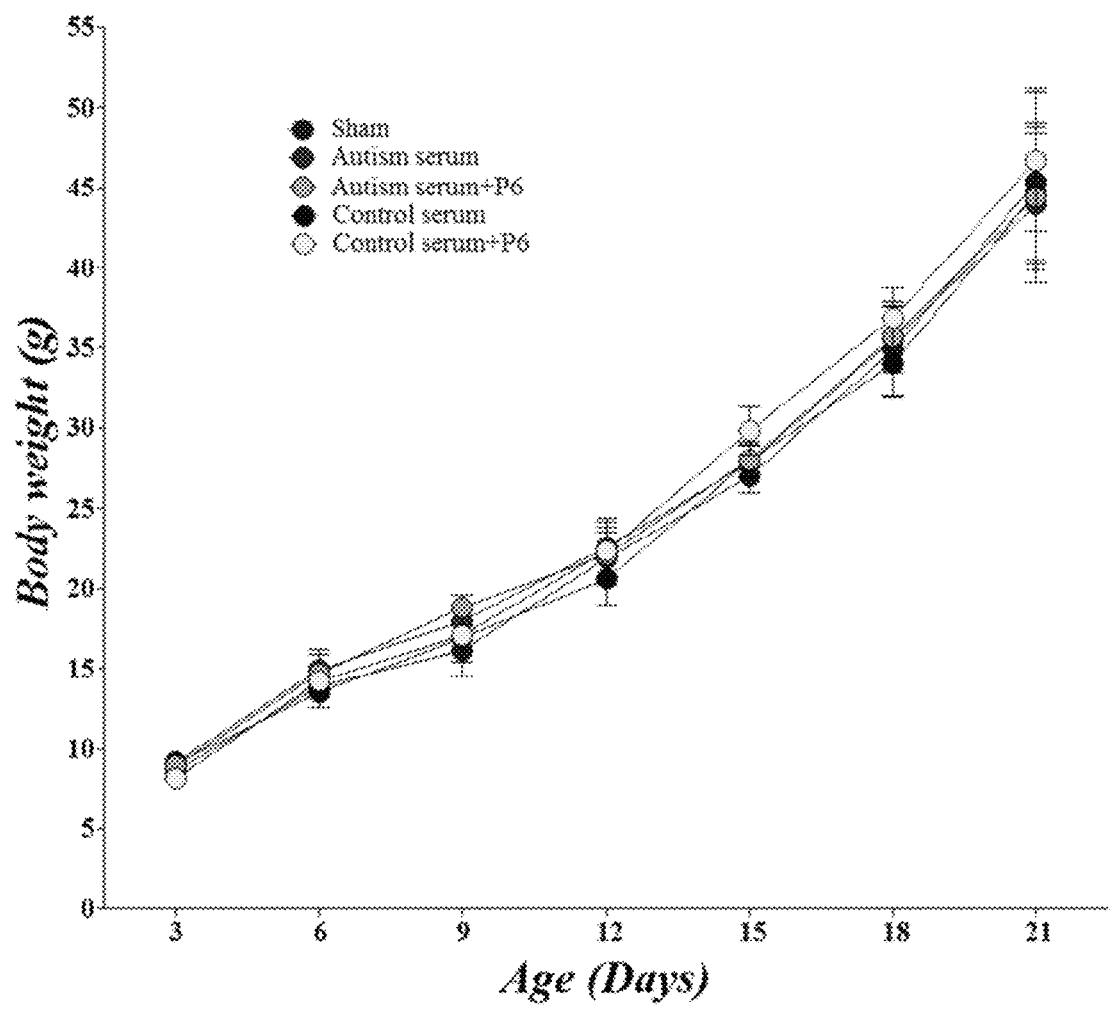

FIG. 7 is a line graph of the body weight evaluation of young Wistar rats from postnatal day 3 to 21. Data are presented as mean+S.E.M. based on sham (n=17), autism serum (n=16), autism serum+P6 (n=17), control serum (n=16), and control serum+P6 (n=17).

Figure 8A:
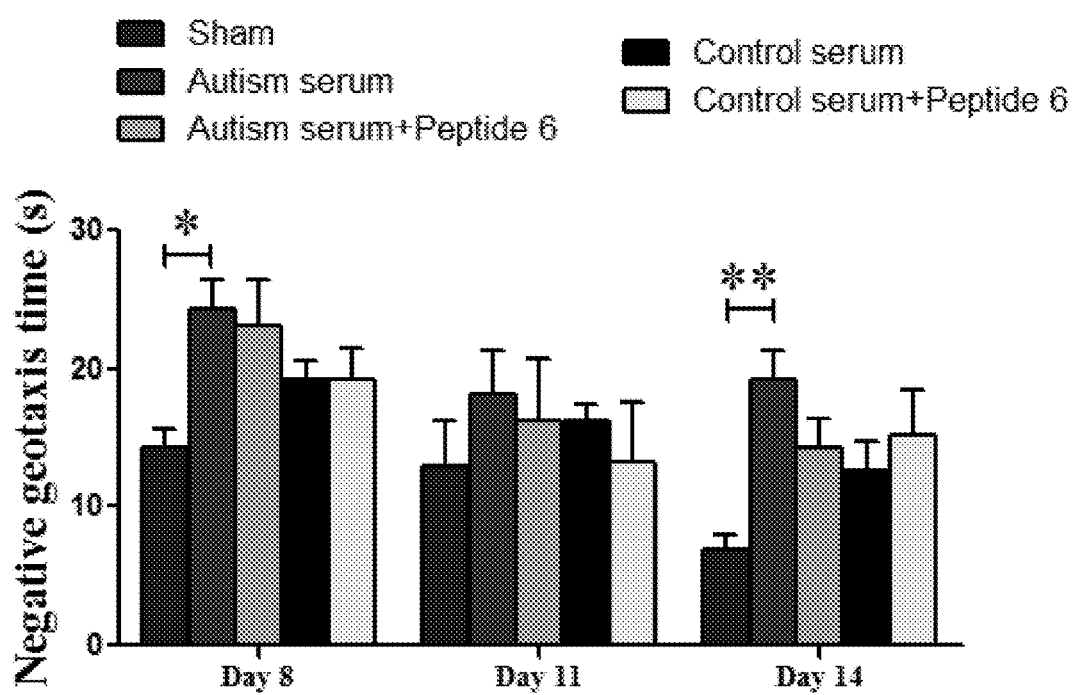
Figure 8B:
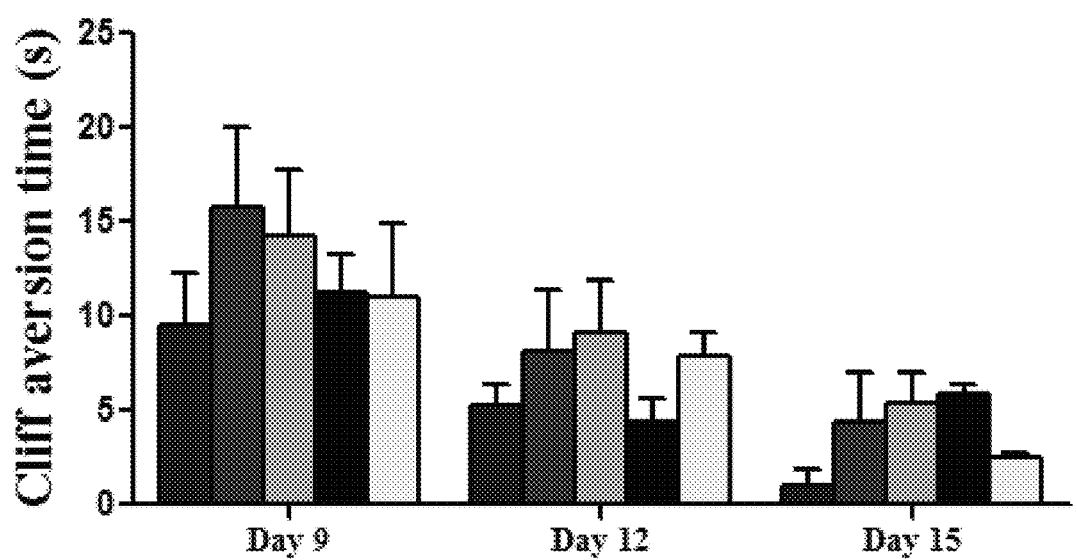

FIGS. 8A and B are bar graphs of the performance in negative geotaxis testing and cliff aversion where FIG. 8B is a graph of negative geotaxis time on days 8, 11, and 14, and FIG. 8A is a graph of cliff aversion on postnatal days 9, 12, and 15. Data are presented as mean+S.E.M. based on sham (n=17), autism serum (n=15-16), autism serum+P6 (n=16-17), control serum (n=15-16), and control serum+P6 (n=16-17) with *p<0.05, p<0.01, and *p<0.001 (ANOVA with Bonferroni's post-hoc test and/or Student's t-test).

Figure 9A:
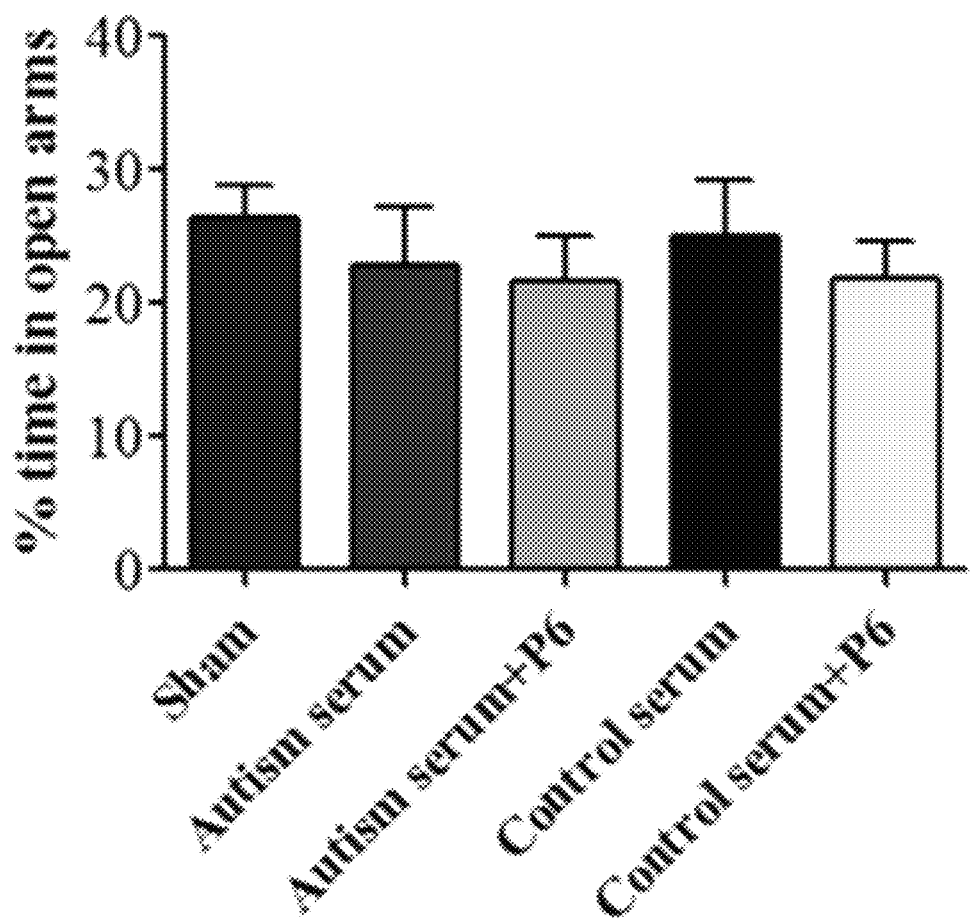
Figure 9B:
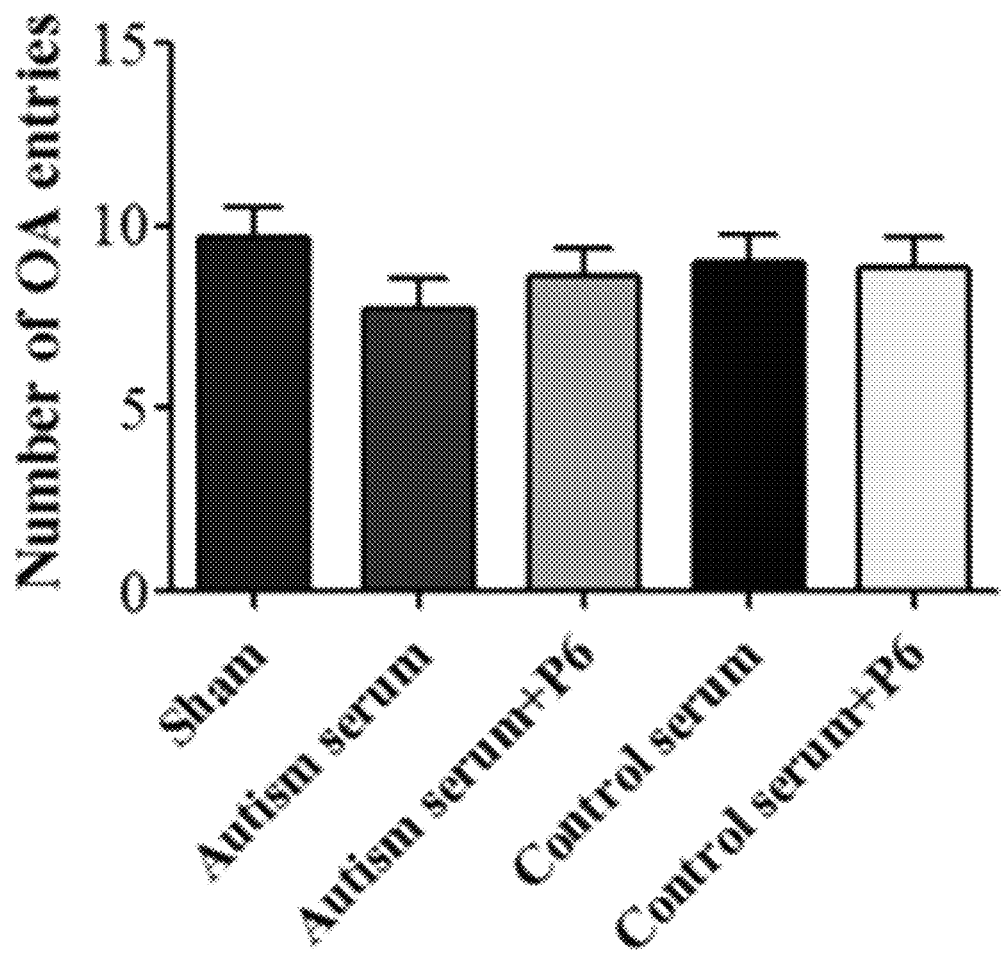
Figure 9C:
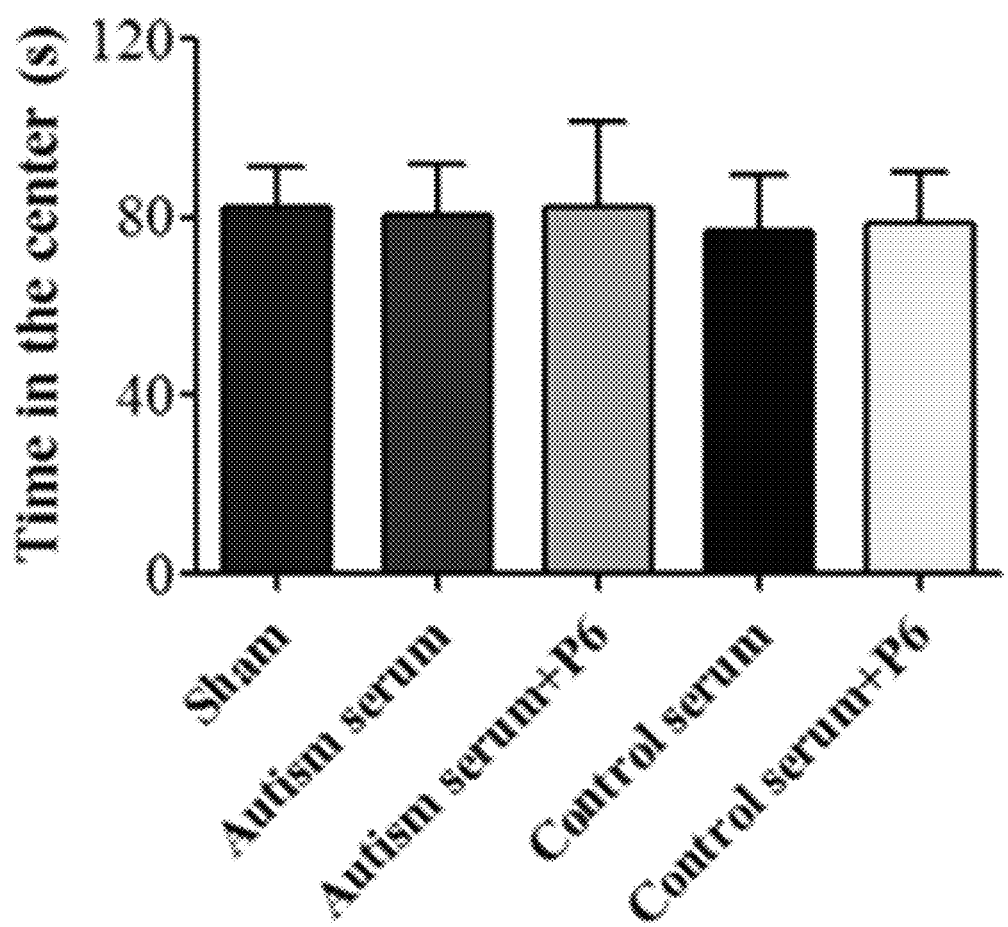
Figure 9D:
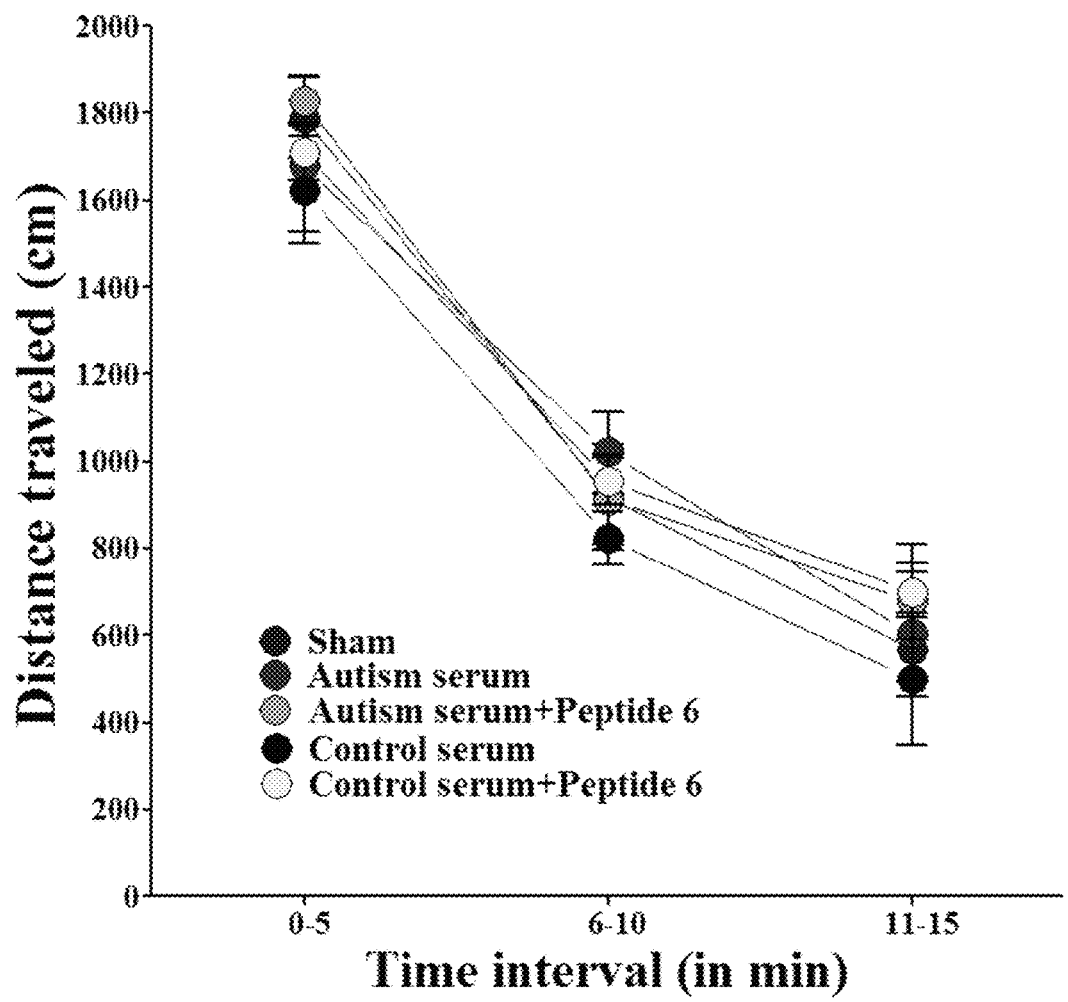
Figure 9E:
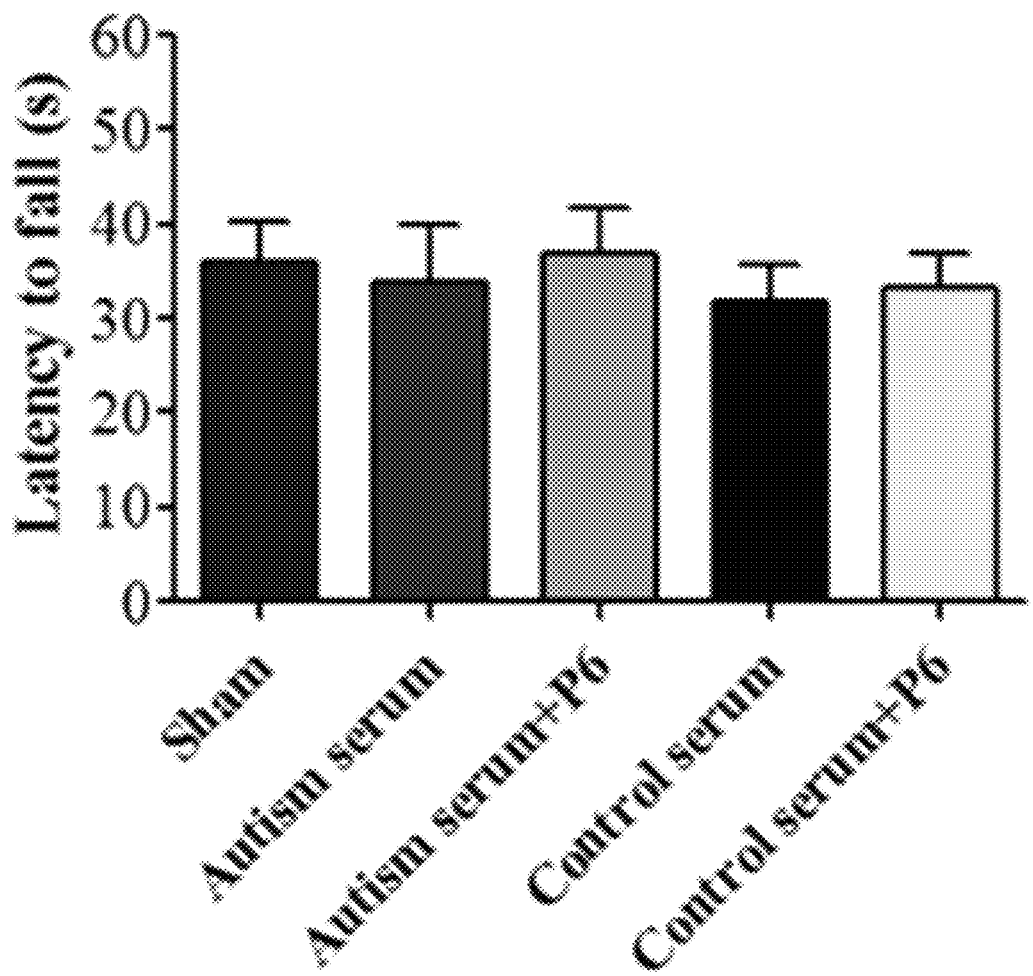
Figure 9F:
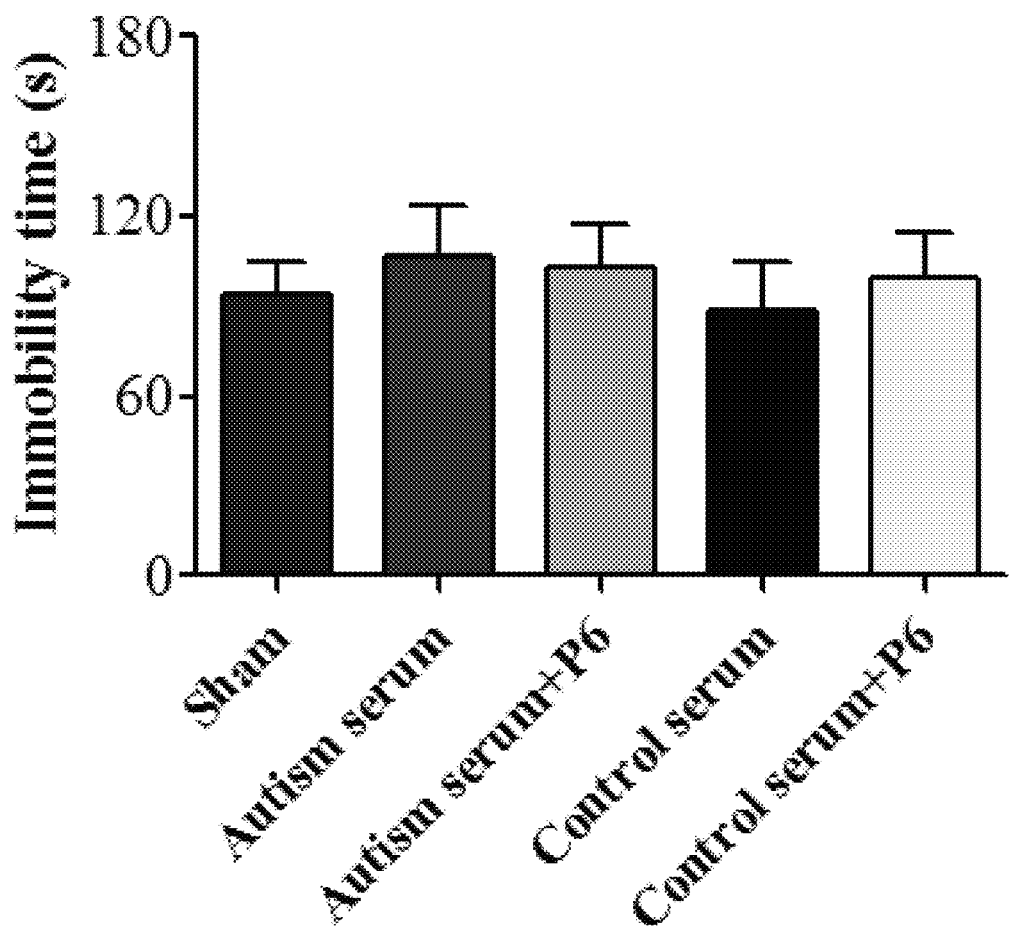

FIG. 9A through 9F are graphs of the general behavioral characterization in young Wistar rats injected intracerebroventricularly on P0.5 with sham or 2% autism or control serum with or without 20 nM P6. Anxiety-like behaviors were evaluated by, as seen in FIG. 9A, percent time in the open arm, OA (ANOVA, p=0.8551), as seen in FIG. 9B, the number of entries to OA (ANOVA, p=0.5295) in an elevated plus maze on postnatal day 18-19, and, as seen in FIG. 9C, the time in the center (ANOVA, p=0.9975) in an open field arena on postnatal day 19-20. There was a trend towards decreased number of OA entries in autism serum injected young rats (sham group vs autism serum group, Bonferroni's post hoc test, p>0.05, Student's t-test, p=0.08). FIG. 9D is a graph of the spontaneous locomotor and exploratory activities assessed in open field [repeated measures 2-way ANOVA, group effect, F=0.34 (8, 219), p=0.9513]. FIG. 9E is a graph of the motor strength evaluated by latency to fall in prehensile traction test on postnatal day 24-25 (ANOVA, p=0.9332). FIG. 9F is a graph of the behavioral despair and depression-like behavior analyzed by immobility time in forced swim test on postnatal day 24-25 (ANOVA, p=0.9410). Data are presented as mean+S.E.M. based on sham (n=15-17), autism serum (n=15-17), autism serum+P6 (n=15-17), control serum (n=15-17), and control serum+P6 (n=15-17).

DETAILED DESCRIPTION OF THE INVENTION

The present invention involves the use of an 11-mer peptide, Peptide 6 (P6), which is blood-brain barrier (BBB) permeable, has a plasma half-life of over 6 hr, and does not cause adverse effects associated with the full-length protein in mice or rats, to treat autism. This CNTF derived small peptide mimetic exerts a beneficial effect on neurogenesis, neuronal and synaptic plasticity, and cognition via inhibition of LIF signaling pathway and elevation of BDNF level by increasing its transcription. To establish the efficacy of the use of Peptide 6 to treat autism, a series of experiments were performed and show that: (i) sera from children with autism cause neurodegeneration and increased oxidative stress in embryonic day 18 mouse primary neuronal cultures; (ii) intracerebroventricular injection of autistic sera within hours after birth produces characteristic autistic behavioral phenotype in young rats; and (iii) pre-treatment with P6 is neuroprotective to autistic sera-induced changes both in primary neuronal cultures and in vivo in rats.

EXAMPLE

Materials and Methods

Sera from Children with Autism and from Healthy Controls

Table 1 below summarizes the general clinical profiles of 22 pairs of children with autism and healthy controls whose sera were screened in in vitro studies, and Table 2 below provides details of the 3 pairs of these autism and control subjects whose sera were used for further in vitro and in vivo investigations. The diagnosis of autism was made using Autism Diagnostic Observation Schedule-Generic (ADOS-G) and the Diagnostic and Statistical Manual of Mental Disorders, 4th edition (DSM-IV).

TABLE 1

Characterization of serum donors initially screened

| Diagnosis (DSM-IV; ADOS-G) | Autism | Control |
|---|---|---|
| Number of donors (M/F) | 22 (15/7) | 22 (13/9) |
| Mean Age (± S.E.M.) | 4.96 ± 0.11 | 5.17 ± 0.195 |
| Age range | 4.1-6 | 3.76-6.4 |
| Autism Diagnostic Interview-Revised Scale (ADI-R) | | |
| QA in reciprocal social interaction | 17.45 ± 1.47 (7-28)[a] | N/A |
| QA in communication | 12.14 ± 0.58 (7-20) | N/A |
| Restricted, repetitive and stereotyped behavior | 5.09 ± 0.41 (3-12) | N/A |
| Verbal Adaptive Behavior Scale | | |
| Communication | 58.86 ± 3.9 (40-106) | N/A |
| Daily living skills | 59 ± 3.01 (36-104) | N/A |
| Socialization | 58.14 ± 1.81 (49-78) | N/A |
| Motor | 61.41 ± 2.93 (41-93) | N/A |

[a]Range of the results; N/A, Not applicable

Further confirmation of the diagnosis was performed with Autism Diagnostic Interview-Revised (ADI-R), an abridged version of ADI administered through interviewing the parents. Additional characterization of the subjects was carried out by Vineland Adaptive Behavior Scale. Blood samples were collected from children in families belonging to the same population based in the New York City (NYC) area and expectedly exposed to similar profile of external environmental factors e.g. air pollution and water contamination. Additional differences owing to variable child care, dietary patterns, inherent household customs and preferences, and various other non-specific environmental factors that may play some role in the development of autism but have not yet been assigned a definitive role were not taken into consideration. The level of IQ was not used as a selection criterion for donors as it is not a definitive diagnostic tool for autism. Control samples were collected from normal children who had siblings with autism but were not related to the probands evaluated in the current study. All autism and control subjects belonged to the ethnic group white. The study subjects did not have any significant history of seizures or gastrointestinal problems, none had received a concomitant diagnosis of fragile X syndrome or Rett syndrome, and none were on antidepressants, neuroleptics, seizure medications, or stimulants. All sera were stored as coded anonymous samples at −80° C. Immediately before experiments, sera were thawed once and used for in vitro and in vivo studies as indicated.

Design and Synthesis of Peptide 6 (P6)

P6, which corresponds to amino acid residues 146-156 of human CNTF, VGDGGLFEKKL (SEQ ID NO: 1) was identified as an active region by epitope mapping of neutralizing antibodies to CNTF. The peptide was synthesized using solid phase peptide synthesis (SPSS) methods, purified by reverse phase HPLC to >96% purity, lyophilized, and characterized via HPLC, NMR, and ESI-MS.

In Vitro Studies

Study Outline

The effects of treatment with the sera from autistic and control children and of P6 were evaluated in the in vitro studies using primary cortical neuronal cell cultures from embryonic day 18 (E18) mouse cortex. The cultured neurons were treated on 4th day in vitro (DIV4, 72 hours after seeding) and their morphology was analyzed on DIV7 (72 hours after treatment). Subsequently, cell death and viability, and oxidative stress were analyzed.

Primary Neuronal Cultures

Primary cortical neuronal cell cultures were prepared from E18 C57BL/6 mice cortex. Briefly, C57BL/6 time pregnant E18 female mice from Charles River labs were anesthetized and killed by cervical dislocation. All studies were performed in accordance with the recommendations in the Guide for the Care and Use of Laboratory Animals of the National Institutes of Health (NIH). The protocol was

TABLE 2

| Diagnosis (DSM-IV; ADOS-G) | Age | Gender | ADIQRS | ADICOM | ADIREPST | CSS | DSS | SSS | MSS |
|---|---|---|---|---|---|---|---|---|---|
| Autism | 5.11 | M | 16 | 14 | 5 | 57 | 58 | 57 | 59 |
| Autism | 4.8 | M | 15 | 13 | 8 | 61 | 63 | 58 | 56 |
| Autism | 4.6 | M | 25 | 12 | 4 | 73 | 65 | 63 | 61 |
| Control | 5 | M | N/A | N/A | N/A | N/A | N/A | N/A | N/A |
| Control | 5.4 | M | N/A | N/A | N/A | N/A | N/A | N/A | N/A |
| Control | 4.8 | M | N/A | N/A | N/A | N/A | N/A | N/A | N/A |

N/A, Not applicable approved by the Institutional Animal Care and Use Committee (IACUC) of the New York State Institute for Basic Research in Developmental Disabilities (Protocol no. 199). Embryos were removed and placed in cold hibernate A (Brain bits, Springfield, Ill., USA), and all following steps were performed in ice-cold hibernate A, using the stereoscopic (dissection) microscope placed in a laminar flow hood. Fetal brains were removed carefully; cerebral cortex was separated, and was dissected and cut into small pieces using microsurgical scissors. The cut tissue was transferred with number 5 forceps to 15 ml tubes containing 0.1% trypsin in versene (Invitrogen Life Technologies, Grand Island, N.Y., USA) and incubated for 15 min at 37° C. followed by inactivation with 10% fetal bovine serum (FBS) in Neurobasal complete medium (Neurobasal Medium supplemented with 2× B-27, 0.3% glutamine, and penicillin/streptomycin 0.1 mg/ml and 0.1 U/ml respectively). After 72 hours, the medium was replaced and supplemented with fresh medium with or without autism or control serum+P6 as described below. All medium components were purchased from Invitrogen Grand Island, N.Y., USA. Cells were maintained in an incubator at 37° C. at 5% $CO_2$/95% atmospheric air.

For recovering the protein, cells were seeded in 6-well plates precoated overnight with 50 µg/ml poly-D-lysine (Sigma-Aldrich, St. Louis, Mo., USA) at a density of $1 \times 10^6$ cells/well. For immunocytochemistry, LDH and oxidative stress assays, cells were seeded onto 8-well chambers or 96-well plates (precoated with poly-D-lysine) at a density of $8 \times 10^4$ cells/well or $7 \times 10^4$ cells/well in 300 or 100 µl Defined Medium, respectively.

Treatment of Cultured Neurons with Sera with or without P6

The cells were cultured for 72 hours prior to beginning of the treatment with a serum alone or serum with P6 or vehicle. Initially, the effect of 22 pairs of autism/control sera were evaluated in 3 separate set of primary cultures. Based on these experiments, 3 pairs of sera with consistent marked effect on neuronal morphology were selected for further experiments. Initially different concentrations of the sera in culture medium (0.1%, 0.2%, 0.5%, and 1%) were evaluated and based on these analyses, a final concentration of 0.2% was chosen for subsequent experiments. Similarly, different concentrations of P6 (0.0005 µM, 0.005 µM, 0.05 µM, and 1 µM) were evaluated.

To study the cytotoxic effects of autism sera and the potential rescue with P6, 72 hours after seeding the cells, the culture medium was replaced with fresh medium containing different concentrations of P6. The P6 was dissolved in water from which necessary amount was added directly to the culture medium to achieve the desired final concentration. Three hours after the pre-treatment with P6, sera from autistic or control children were added to the culture medium already containing P6 to achieve a final concentration of sera to be 0.2%. Few wells in each plate or chamber were left vehicle treated only to serve as controls. The treatment continued for a total of 72 hours after which light microscopic evaluation of cultured neurons was performed and low and high magnification images were captured using Nikon digital camera system for digital sight, DS-Fi 1 coupled with Nikon Labophot microscope. After a total of 6 days-in-vitro, immunohistochemical analysis and LDH and oxidative stress assays were performed in different set of experiments.

LDH Assay for Cell Death and Cell Viability

Cell death and cell viability were analyzed using the LDH cytotoxicity assay kit (Promega, Madison, Wis., USA), following manufacturer's instructions. Cell death (LDH release at OD 490 nm) and cell viability (percent of control) were plotted separately.

Oxidative Stress Assays

DCFH-DA for Evaluating the Generation of Free Radicals

Dichlorofluorescein (DCF) fluorescence assay was used to determine the intracellular production of reactive oxygen species as described previously (Muthaiyah et al., 2011). Briefly, the primary neuronal cells were treated with the cell permeable 2,7-dichlorofluorescein diacetate, DCFH-DA (Sigma, St. Louis, Mo., USA) which is converted into 2',7'-dichlorofluorescein. The 2',7'-dichlorofluorescein interacts with intracellular peroxides to form a highly fluorescent compound. The medium was removed three days after serum with or without Peptide 6 treatment and cells were washed with Hank's Balanced Solution, HBSS (Invitrogen, Camarillo, Calif., USA). The cells were incubated with DCFH-DA (10 µM) for 30 min and then washed with HBSS solution two times. DCF fluorescence was quantified (excitation wave length=485 nm, emission wave length=530 nm) using a fluorescence multi well plate reader (Spectra Max M5, Molecular Devices, Sunnyvale, Calif., USA).

TBARS Assay for Evaluation of Lipid Peroxidation

Lipid peroxidation was assessed by determining the level of thiobarbituric acid reactive substance (TBARS) in primary neuronal cell lysates. Cultured neurons were lysed in lysis buffer (50 mM HEPES, pH 7.5, 1% Triton X-100, 50 mM NaCl, 5 mM EGTA, 50 mM sodium fluoride, 20 mM sodium pyrophosphate, 1 mM sodium vanadate, 2 mM PMSF, and 8 mM diisopropylfluorophosphate) containing 0.05% butylated hydroxytoluene (BHT). The 100 µl of cell lysate was added to 200 µl ice-cold 10% trichloroacetic acid (TCA) on ice for 15 min to precipitate protein. Precipitated samples were centrifuged at 2200×g for 15 min at 4° C. Supernatants were mixed with an equal volume of 0.67% thiobarbituric acid and then boiled for 10 min. Once cooled, the absorbance was read at wave length 532 nm on an absorbance plate reader (Spectra Max M5, Molecular Devices, Sunnyvale, Calif., USA). Malonyldialdehyde (MDA, an end product of peroxidation of polyunsaturated fatty acids and related esters and a marker of lipid peroxidation) content was calculated using a molecular extinction coefficient for MDA of $2.56 \times 10^5$.

Immunocytochemistry of Cultured Neurons for β-III-Tubulin Staining

After 3 days of treatment, cells seeded in 8-well chambers were fixed in 4% paraformaldehyde (Electron Microscopy Sciences, PA, USA) for 30 min at room temperature, and then washed two times in PBS for storage at 4° C. prior to staining Cells were permeabilized in 0.05% Triton-X-100 in PBS for 20 min at 25° C., washed in PBS 3×10 min, and then incubated in blocking buffer (1% BSA w/v, 0.2% Triton-X-100 v/v in PBS) for 45 min at 25° C. The cells were then incubated with rabbit polyclonal anti-Tuj-1, β-III-tubulin (1:200, Covance, Emeryville, Calif., USA) antibody in blocking buffer at 4° C. overnight. The cells were washed three times for 10 min in PBS and then incubated with fluorescently-labeled CY3-conjugated goat anti-rabbit secondary antibody (1:500, Jackson Laboratory, Maine, USA) diluted in blocking buffer for 2 h at 25° C. in the dark. The cells were washed 3×10 min in PBS and 24×60 mm cover glass (Brain Research Laboratories, Newton, Mass., USA) was mounted with Vectashield anti-fade mounting medium (Vector Laboratories Inc., Burlingame, Calif., USA) and sealed with nail polish. The slides were examined using 20× and 40× objectives of a Nikon 90i fluorescent microscope equipped with Nikon C1 three-laser confocal system and a Nikon DS U1 digital camera, and analyzed with EZ-C1 Viewer Image software, Version 6.0.

Western Blots of Human Serum Samples for Neurotrophic Factors Levels

For Western blots to evaluate the levels of various neurotrophic factors in sera samples, the serum samples were diluted in loading buffer and loaded as appropriate assuming normal human serum protein concentration to be ~80 µg/µL. SDS-PAGE 10% or 12.5% gels were employed followed by transfer of separated proteins on 0.45 μm PVDF membranes (Pall, Pensacola, Fla., USA) for Western blots. The following primary antibodies were used at the indicated dilutions: rabbit polyclonal anti-CNTF, FL-200 (1:500, Santa Cruz Biotechnology, Santa Cruz, Calif., USA); rabbit polyclonal anti-BDNF, N-20 (1:1000, Santa Cruz Biotechnology, Santa Cruz, Calif., USA); goat polyclonal anti-LIF, N-18 (1:500, Santa Cruz Biotechnology, Santa Cruz, Calif., USA); rabbit polyclonal anti-NGF, M-20 (1:1000, Santa Cruz Biotechnology, Santa Cruz, Calif., USA); and rabbit polyclonal anti-FGF2, 147 (1:500, Santa Cruz Biotechnology, Santa Cruz, Calif., USA).

Blots were blocked for 1 hr at 37° C. in TBST (0.05% Tween 20 in TBS) containing 5% w/v blotting grade dry milk (Bio-rad, Hercules, Calif., USA), incubated in primary antibody in blocking buffer overnight at 4° C., washed 3 times for 10 min in TBST at room temperature, followed by incubation with secondary antibody i.e. peroxidase-conjugated anti-rabbit or anti goat IgG (Jackson ImmunoResearch Laboratories, West Grove, Pa., USA) diluted in blocking buffer. Blots were washed 3×10 min in TBST and immunoreactive protein bands were visualized with enhanced chemiluminescence (ECL) reagents (Pierce, Rockford, Ill., USA). The ECL films of the blots were scanned and analyzed using Multi Gauge software version 3.0 (Fujifilm, Tokyo, Japan). For loading control, the blots were developed with rabbit polyclonal antibody to GAPDH (1:1000, Santa Cruz Biotechnology, Santa Cruz, Calif., USA).

In Vivo Studies in Rats

Study Outline

To study the effect of sera and P6 in the in vivo setting, new born Wistar rat pups (within 24 hours of birth) were injected intracerebroventricularly with sera (final concentration ~2%) from autism or control children with or without P6 (final concentration ~20 nM). The same 3 pairs of sera which showed consistent marked effects in in vitro studies were used for in vivo evaluation. Following injections, a battery of behavioral tests including recording of ultrasonic vocalizations and neonatal developmental milestones in pups and evaluation of anxiety, exploration, grooming, social approach/novelty, depression like behavior, and motor strength in young rats were performed. Both male and female pups were studied, and the data were pooled. Corresponding to in vitro investigations, evaluation of neurodegeneration and oxidative stress was carried out in the brain tissue from young rats. The analyses were done in different batches of animals as described below.

Animal Housing and Intracerebroventricular Injections

Normal Wistar rats were purchased from Charles River Laboratories (Germantown, Md., USA) and were bred at the New York State Institute for Basic Research Animal Colony according to the PHS Policy on Human Care and Use of Laboratory animals (revised Mar. 15, 2011). Rats were housed (2/3 animals per cage) with a 12:12-h light/dark cycle and with ad libitum access to food and water. Studies on animals were carried out according to approved protocols from our Institutional Animal Care and Use Committee (IACUC).

On the day of birth, designated as P0.5, pups were individually cryoanesthetized by placing them directly on wet ice for 3 min; the anesthetized pup's head was placed on a non-heat conducting fiber optic light source and the lateral ventricles of the cerebrum were visualized by transillumination. A total of 4 μL of serum with or without P6 (concentrations described below) was injected unilaterally into the lateral ventricle through transcutaneous insertion with a specifically designed fine 10 μL Hamilton syringe with a 30-gauge/0.5 inch/hypodermic cemented needle (Hamilton Syringe Co., Reno, Nev., USA). For injections with sera without P6, 2 μL of autism or control serum was diluted with 2 μL of 0.9% NaCl (physiological saline) to make a final concentration of ~2% serum in rat pup CSF (assuming the total CSF volume in rat pup to be ~100 μL). For injections of sera with P6, 2 μL of autism or control serum was mixed with 2 μL of 1 μM P6 stock solution (final concentration of P6 in rat pup CSF ~20 nM). For sham injection group, 4 μL of 0.9% NaCl was injected. From each litter, equal numbers of pups were injected for each group (sham, autism serum, control serum, autism serum+P6, control serum+P6) to diminish the litter effect among study groups. After intracerebroventricular injections (i.c.v.), pups were returned to the mother, and later behavioral tests were carried out.

To avoid the potential confounding effects of previous handling, different badges of animals were used for ultrasound vocalizations and for neurobehavioral development and young rat behavior.

Behavioral Procedures

General Examination

The physical state and condition of the rats were carefully examined throughout the study period by evaluating grooming, posture, physical state, and clasping reflex. Body weight was recorded daily during the initial 21 days (till weaning).

Neurobehavioral Development

Examination of neurobehavioral development in rodents is an important study tool to model neurodevelopmental disorders like autism and Down's syndrome, which are characterized by growth retardation and delays in the appearance of developmental milestones. In mice and rats, the early postnatal period is characterized by a spurt of brain growth, synaptogenesis, myelination, and the development of motor and sensory abilities. Thus, evaluation of neurobehavioral development in rodents provides an opportunity to track the ontogeny of the nervous system through examination of neurological reflexes, early motor behavior including muscular strength and coordination, and developmental signs.

Evaluation of neurobehavioral development was performed following procedures described in the relevant literature. Examination was started on postnatal day 1 and was carried out until postnatal day 17 (or until the appearance of developmental milestone/reflex) daily between 12:00-15:00 in a set up made specifically for the purpose in the behavior lab. Weight was also recorded each day. The rat pups were evaluated for the following neurological signs, reflexes, and developmental milestones.

Surface Righting

Surface righting is a measure of labyrinthine and body righting mechanisms, motor strength and coordination. Each rat pup was placed on its back with the experimenter's fingers holding the head and the hind body. The pup was released gently and the time taken in seconds to turn over with all four paws placed on the surface of the table was measured. The test was stopped if the pup did not turn over within maximum 30 s. It was measured once daily until the rat pup could right itself in less than 1 s for two consecutive days. The data for the day of first appearance of the reflex was analyzed.

Negative Geotaxis

Negative geotaxis measures labyrinthine reflex and body righting mechanisms, strength, and motor coordination (Hill et al., 2007). Each rat pup was placed head down on a square of screen mounted at an angle of 450. The time taken by the pup to turn around 180° to the head up position was recorded. The test was stopped if the pup did not turn around within 30 s. If the rat pup lost grip and slipped on the screen, it was replaced at the start point once. The test was repeated daily until the rat pup could perform appropriately in less than 30 s for two consecutive days. The first day of appearance of the reflex was analyzed for different groups.

Cliff Aversion

The cliff aversion test is a measure of labyrinthine reflex function, feel sensitivity, and motor strength and coordination (Hill et al., 2007; Toso et al., 2008). The rat pup was placed on the edge of a cliff (smooth box) with the snout and fore limbs over the edge, and the time taken in seconds to turn and crawl away was recorded. The test was repeated daily until the rat pup could perform appropriately in less than 30 s for two consecutive days. The first day of appearance of the reflex was analyzed for different groups.

Rooting Reflex

The rooting reflex is a sensory tactile reflex also requiring motor coordination; it is mediated by the trigeminal nerve (cranial nerve V) (Hill et al., 2007; Toso et al., 2008). A cotton swab was applied from front to back along the side of the head and the head turning response towards this tactile stimulus was recorded. The test was continued daily till the pup responded correctly for 2 consecutive days.

Ear Twitch Reflex

A measure of sensory tactile reflex, ear twitch test was performed daily by gently brushing the pulled out end of cotton swab against the tip of the ear; a positive reflex consisted of rat pup flattening the ear against the side of the head (Hill et al., 2007). The test was repeated daily until the pup responded correctly for 2 consecutive days.

Eye Opening

A developmental milestone, the first day of opening of both eyes was recorded.

Air Righting

Like surface righting, air righting is also a measure of labyrinthine and body righting mechanisms and motor coordination. The rat pup was held upside nearly 12 cm above the soft bedding of a cage and was released; the test was considered positive on the day when the pups land with all its four paws placed on the surface of the bedding. The test was repeated daily until the pup responded correctly for 2 consecutive days.

Fore Limb Grasp

A measure of strength, fore limb grasp test was performed by holding a rat pup with its forepaws grasping a string fixed from one end to the other end of the cage nearly 12 cm above the bedding. The pup was released, and the amount of time the pup spent grasping the string was recorded. The test was considered positive when the pup kept on grasping the string with fore limb for >1 s; it was repeated every day until performed correctly for 2 consecutive days (Hill et al., 2007).

Fore Limb Placing

A measure of placing reflex development which measures sensory and motor coordination, fore limb placing test was performed by touching the dorsum of the paw with the edge of the table with the animal suspended; the first day of raising the forepaw and placing on the surface of the table was noted. The test was repeated daily until the pup responded correctly for 2 consecutive days.

Auditory Startle

The auditory reflex was evaluated by clapping within 10 cm of the rat pup and the first day of the startle response was recorded. The test was repeated daily until the pup responded correctly for 2 consecutive days.

Ultrasonic Vocalizations

Ultrasonic vocalizations (USVs) have been widely used for behavioral phenotyping of rodent models of neurodevelopmental disorders. USVs emitted by infant rats have been reported to be a reliable index of emotional development and communicative behavior. Infant rats emit USVs in many different situations including isolation from dam and littermates, physical manipulation, and thermal and olfactory challenges. Isolation induced USVs are considered to be distress vocalizations and have been shown to elicit maternal searching and retrieval. In rat pups, USVs in response to isolation distress are evident usually on the first postnatal day; they increase in number and intensity toward the beginning of second week of life and then abruptly disappear by the end of second week. USVs produced by rat pups typically fall in the range 20-50 KHz.

USVs were recorded daily from 2nd to 11th postnatal day in experimental animals based on the baseline measurements obtained initially with 12 untreated Wistar rat pups during a 5 minute session daily from postnatal day 1 to 15. On each day of testing, pups were isolated one-by-one from their home cage and placed into an empty rectangular glass container (length×width×height=10 cm×7.5 cm×6 cm) located inside a sound-attenuating Styrofoam box mounted with a bat detector. Three such systems were used at the same time, thus, allowing recording of USVs emitted by 3 pups simultaneously. Each box was closed to prevent the detectors from detecting sounds that were not derived from the pup inside. The temperature of the room was fixed at 22+/−1° C. The frequency detectors were set to 40 KHz, which is within the vocalization range of isolation induced USVs produced by rat pups. The frequency detectors were attached via a Noldus box to a computer equipped with Ultravox software, which detected the number and duration of USVs. Minimum USV duration (on time; shortest time of the noise to be counted as a call) was set to be 10 ms. For a call to be considered independent, an off time (minimum time silent before a new noise is counted as a call) of 5 ms was set to be required. No differences were observed in the patterns of calling between male and female pups; thus, the data was pooled together across gender.

Elevated Plus-Maze

The level of anxiety in 18-19 day old young rats was evaluated by elevated plus maze testing. The elevated plus maze comprised of four arms (30×5 cm) connected by a common 5×5 cm center area. There were two opposite facing open arms (OA) and the other two facing arms enclosed by 20-cm high walls (CA). The entire plus-maze was elevated on a pedestal to a height of 82 cm above floor level in a room separated from the experimenter. The anxiogenic feature of the light for rats was maintained by ambient luminosity at 60 Lux which is considered to be non-anxiogenic. The young rat was placed onto the central area facing an open arm and was allowed to explore the maze for a single 8 min session. Between each rat, the feces were removed from the maze and the maze floor was wiped with paper towel soaked with 70% ethanol to avoid any urine or scent cues. For each rat, the number of OA and CA entries and the amount of time spent in each arm were recorded by a video tracking system (ANY-Maze software, version 4.5, Stoelting Co., Wood Dale, Ill., USA). The anxiety-like behavior was evaluated by calculating the percentage of time spent in OA [OA/(OA+CA)×100]; OAs are more anxiogenic for rodents than CAs.

Open Field

Exploratory behavior was analyzed by allowing 19-20 day old young rats to freely explore an open field arena in a single 15 min session. The testing apparatus was a classic open field consisting of a 50×50 cm PVC square arena surrounded by 40 cm high walls. The open field was placed in a room separated from the investigator and was surmounted by a video camera connected to a computer tracking animals using a video tracking system (ANY-Maze software, version 4.5, Stoelting Co., Wood Dale, Ill., USA). The parameters analyzed included time spent in the center of the arena and total distance traveled which are measures of anxiety and exploratory activity, respectively.

Grooming, Social Approach, and Social Novelty Test

Grooming, social approach, and social novelty were analyzed using a 3-chamber box in 21-23 day old young rats. The rectangular testing box consisted of clear plastic divided into three adjacent chambers (each 20 cm long, 40 cm wide and 22 cm high) and connected by open doorways (7 cm wide and 6.4 cm high). Social approach behaviors were tested in a single 35-min session, divided into 4 phases. This experiment had two habituation phases (center and all 3 chambers) followed by two testing phases (sociability and novelty). The first test or social approach phase of the test compared the preference for a social stimulus versus an inanimate object. The second test or social novelty phase of the test compared the preference for a now familiar social stimulus to a novel social stimulus.

The subject young rat was acclimated to the apparatus for 5 min in the center chamber (phase 1), and then for an additional 10 min with access to all 3 empty chambers (phase 2). The subject was then confined to the middle chamber, while the novel object (an inverted wire cup, Galaxy Cup, Kitchen Plus, Streetsboro, Ohio) was placed into one of the side chambers, and the stranger mouse (stranger 1), inside an identical inverted wire cup, was placed in the opposite side chamber. Age and gender matched Wistar rats were used as the stranger rat. The location (left or right) of the novel object and stranger rat alternated across subjects. The chamber doors were opened simultaneously, and the subject had access to all 3 chambers for 10 min (phase 3). After this, the fourth 10-min session provided a measure of preference for social novelty (phase 4). The subject rat was gently guided to the center chamber, the doors closed, and the novel object removed, and a second novel rat (stranger 2) was placed in the side chamber. The chamber doors were opened simultaneously, and the subject again had access to all 3 chambers for 10 min. The fourth 10-min phase provided a measure of recognition and discrimination. Video tracking with ANYmaze (Stoelting, Inc.; Wood Dale, Ill.) automatically scored the time spent in each of the 3 chambers, frequency and duration of grooming episodes; frequency and duration of sniffing episodes; and number of entries into each chamber during each phase of the test. Animals used as strangers were age and gender matched rats habituated to the testing chamber for 30-min sessions on 3 consecutive days and were enclosed in the wire cup to ensure that all social approach was initiated by the subject rat. An upright plastic drinking cup weighed down with a lead weight was placed on top of each of the inverted wire cups to prevent the subject rat from climbing on top. Ambient luminosity was maintained at 60 Lux.

Forced Swim Test (Behavioral Despair Test)

Depression-like behavior was analyzed using behavioral despair test (Forced swimming test, FST, or Porsolt test) in 24-25 day old young rats. The FST assesses the tendency to give up attempting to escape from an unpleasant environment, whereby fewer attempts are interpreted as behavioral despair. The test was conducted in a single 6-minute session. Briefly, test rats were transported to a separate treatment room at least 1 hour before testing. The rat was placed in a cylinder of water (23 cm high, 11.5 cm diameter) filled to a depth of 16 cm that was meticulously maintained at 24+/−1° C. The time mice spent floating on the water (immobility time, sec) during 6 minutes as well as latency (sec) to the first immobility episode were manually observed by the investigator. After the testing, the animal was dried briefly with a towel and returned to its home cage. As is standard in the literature, all rats were exposed to the forced swim stressor in a cylinder that had been freshly cleaned and disinfected prior to the session. An animal was considered immobile when floating motionless or making only those movements necessary to keep its head above the water surface. Swimming was defined as vigorous movements with forepaws breaking the surface of the water. Finally, the data was analyzed for immobility time (sec) for the last 4 min of the 6 min testing session.

Prehensile Traction Test

Prehensile traction force was evaluated measuring fall latency of the 24-25 day old young rats suspended with forepaws from a string suspended 60 cm from a padded surface. The latency for the rat to fall from the string was measured up to 60 s.

Tissue Processing

After completion of behavioral testing, the 26-27 day old young rats were perfused and brain tissue was collected for immunohistochemical and biochemical analysis. Animals were anesthetized with an overdose of sodium pentobarbital (125 mg/kg) and transcardially perfused with 0.1 M phosphate buffered saline (PBS). After perfusion, the brains were removed from the skull immediately. The left hemisphere was dissected into hippocampus, cerebral cortex, cerebellum, and brain stem, immediately frozen on dry ice, and then stored in—800 C ultrafreezer till used for biochemical analysis. The complete right hemisphere was immersion fixed in 4% paraformaldehyde in 0.1 M PBS for 24-48 hours, followed by cryoprotection in a 30% sucrose solution at 40° C. overnight. Later, the 40-µm-thick sagittal sections were cut on a freezing microtome. The sections were stored in glycol anti-freeze solution (Ethylene glycol, glycerol, and 0.1 M PBS in 3:3:4 ratio) at −20° C. until further processing for immunohistochemical staining.

Western Blot Analysis of Rat Brain Tissue

The tissue from left cerebral cortex from each rat was homogenized in a Teflon-glass homogenizer to make 10% (w/v) homogenate. The pre-chilled homogenization buffer contained 50 mM Tris-HCl (pH 7.4), 8.5% sucrose, 2 mM EDTA, 2 mM EGTA, 10 mM b-mercaptoethanol plus the following protease and phosphatase inhibitors: 0.5 mM AEBSF, 10 µg/ml aprotinin, 10 µg/ml leupeptin, 4 µg/ml pepstatin, 5 mM benzamidine, 20 mM beta-glycerophosphate, 50 mM sodium fluoride, 1 mM sodium orthovanadate, and 100 nM okadaic acid. Protein concentration of each brain homogenate was estimated by modified Lowry assay (Bensadoun & Weinstein, 1976). The tissue homogenates were boiled in Laemmli's buffer for 5 min, and then subjected to 12.5% SDS-polyacrylamide gel electrophoresis (PAGE), followed by transfer of separated proteins on 0.45 µm Immobilon-P membrane (Millipore, Bedford, Mass., USA). The following primary antibody was used: rabbit polyclonal anti-BDNF, N-20 (1:1000, Santa Cruz Biotechnology, Santa Cruz, Calif., USA); rabbit polyclonal anti-CNTF, FL-200 (1:500, Santa Cruz Biotechnology, Santa Cruz, Calif., USA); and rabbit polyclonal antibody to GAPDH (1:1000, Santa Cruz Biotechnology, Santa Cruz, Calif., USA) as loading control. The blots were developed and quantified as described before.

Fluoro-Jade C Labeling for Neurodegeneration in Rat Brain Tissue

Fluoro-Jade C staining was performed as described previously (Schumed et al, 1997; Wang et al, 2013) on 4-5 sections/animal and minimum of 6 animals/group (including 2 animals for each serum sample injected). Briefly, free floating brain sections were washed in large volumes of distilled water, followed by 3 min incubation in 100% alcohol, 1 min in 70% alcohol, 1 min in 30% alcohol, and a 1 min wash in distilled water. The tissue sections were then incubated in 0.06% potassium permanganate solution for 15 mins with gentle shaking followed by 1 min wash in distilled water. The staining solution contained a 0.001% Fluoro-Jade C (Chemicon Millipore, Temecula, Calif.) in 0.1% acetic acid. After 30 min incubation in Fluoro-Jade C solution with gentle shaking, the sections were washed three times for 1 min in distilled water followed by three 2 min rinses in xylene. The sections were mounted and cover slipped using DPX Fluka (Milwaukee, Wis.). Maximum projection images were generated based on confocal z-stacks using Nikon 90i fluorescent microscope equipped with Nikon C1 three-laser confocal system and a Nikon DS U1 digital camera. Images were filtered with a predetermined threshold using NIH Image J (v.1.46r) to create a binary image identifying positive and negative labeling and percentage of area occupied by Fluoro-Jade C positive labeling was calculated. Mean positive label values were averaged from 3-4 non-overlapping representative fields (40× objective) from cerebral cortex. The data from serum+Peptide 6 treatment groups was calculated as percentage of sham treated group.

Measurement of oxidative stress using 8-OHdG in young adult rat brain tissue Immunohistochemistry for the DNA oxidative damage marker, 8-hydroxy-2'-deoxyguanosine (8-OHdG) was performed on free-floating sections and every tenth brain section was chosen for quantification. For quantification, 5-6 brain sections of minimum 6 animals per group (including 2 animals for each serum) were analyzed. The mouse monoclonal 8-OhdG primary antibody (1:500, QED Biosceince Inc., San Diego, Calif.) and Alexa 488-conjugated goat anti-mouse IgG secondary antibody (1:500, Molecular Probes, Carlsbad, Calif., USA) were used. For quantification of 8-OHdG positive cells in cerebral cortex, four non-overlapping representative fields were imaged using 40× objective and maximal projection images were generated as described before. The number of positive cells in each cerebral cortex high power field (hpf) were counted and were averaged.

Statistical Analysis

Statistical analyses were performed using SPSS version 17.0 (© SPSS Inc., 1989-2007, Chicago, Ill., USA) and GraphPad Prism version 5.0 (GraphPad software inc., La Jolla, Calif., USA). Data are presented as mean+S.E.M. The normality of the data was determined using Kolmogorov-Smirnov test. The analysis involving multiple groups was done using one-way ANOVA followed by Bonferroni's post-hoc test. Student's t-test was used for all other comparisons (including inter-group comparisons for sera/peptide treatment effect). The statistically significant outliers excluded from the analysis were identified using Grubb's test. For all purposes, $p<0.05$ was considered as statistically significant.

Results

Sera from autistic children induce cell death and oxidative stress which can be rescued by P6 pre-treatment in mouse primary cultured cortical neurons Previously, sera from individuals with autism which possess abnormal levels of various regulatory elements were shown to alter the development and proliferation of human neural progenitor cells (NPCs) and to possess autoantibodies against human NPCs (Mazur-Kolecka et al., 2007; Mazur-Kolecka et al., 2009; Mazur-Kolecka et al., 2013). Mouse primary cultured cortical neurons grown for 72 hours in medium supplemented with sera from autistic children either formed neurospheres like colonies of cells with sharp spinous processes or multiple small cells with markedly short processes and decreased cell density as compared to the untreated or control sera treated cell cultures both as observed by phase contrast microscopy and by immunostaining for neuronal marker, β-III-tubulin (FIG. 1A). Primary cultured neurons grown in the presence of sera from normal healthy controls revealed no gross morphological changes and only a few neurosphere like colonies were observed. Pretreatment with 1 µM P6 for 3 hours prevented the decrease in neurite length and cell density caused by the autism sera (FIG. 1A). These results were confirmed with 22 pairs of sera (autism and age-matched control, Table 1) in 3 different sets of primary cultures. Further analyses of cell death and oxidative stress were performed in 3 pairs of sera which showed the most marked consistent effect on neuronal morphology. A significant increase in cell death was found by LDH cytotoxicity assay in cultured neurons grown in the presence of sera from autistic children compared to untreated neurons (FIG. 1B; Bonferroni's post-hoc test, $p<0.05$; Student's t-test, $p=0.0039$). Pretreatment with different doses of P6 resulted in a significant reduction in cell death in cultured neurons treated with sera from autistic children (FIG. 1B; P6 0.005 µM, Bonferroni's post-hoc test, $p>0.05$, Student's t-test, $p=0.0183$; P6 0.05 µM, Bonferroni's post-hoc test, $p<0.01$; P6 1 µM, Bonferroni's post-hoc test, $p<0.01$). The cell death was not significantly altered in cultured neurons treated with sera from normal healthy controls compared to untreated controls (FIG. 1B; Bonferroni's post-hoc test, $p>0.05$). Also, the cell death was less in control sera treated neurons compared to neurons treated with sera from autistic children (FIG. 1B; Student's t-test, $p=0.0642$, marginal significance). The neuronal viability, measured as a percentage of viability in untreated cells, was also significantly decreased in autistic sera treated neurons compared to those treated with control sera (FIG. 1C; Bonferroni's post hoc test, $p<0.01$, Student's t-test, $p=0.0076$). P6 pretreatment showed improvement in neuronal viability in autism sera treated cultured neurons (FIG. 1C; P6 0.005 µM, Bonferroni's post-hoc test, $p>0.05$, Student's t-test, $p=0.5619$; P6 0.05 µM, Bonferroni's post-hoc test, $p>0.05$, Student's t-test, $p<0.0765$; P6 1 µM, Student's t-test, $p<0.0964$). Thus, primary cultured neurons grown in the presence of sera from autistic children showed neuronal loss which was rescued by pretreatment with P6.

Primary cortical neurons grown in the presence of autistic sera showed higher levels of oxidative stress as analyzed by DCF-DA assay for free-radical production and TBARS assay for lipid peroxidation both compared to untreated neurons (FIG. 1D, DCF-DA, Bonferroni's post-hoc test, $p<0.001$; FIG. 1E, TBARS, Bonferroni's post-hoc test, $p<0.05$) and to neurons treated with control sera (FIG. 1D, DCF-DA, Bonferroni's post-hoc test, $p<0.001$; FIG. 1E, TBARS, Bonferroni's post-hoc test, $p>0.05$). Pretreatment with P6 resulted in a significant reduction in generation of free-radicals in autistic sera treated neurons (FIG. 1D; P6 0.05 µM, Bonferroni's post-hoc test, $p<0.05$; P6 1 µM, Bonferroni's post-hoc test, $p<0.001$). Even though a trend towards reduction in lipid peroxidation was noted in P6 pretreated autism sera treated neurons but it did not reach statistical significance (FIG. 1E; P6 1 µM, Bonferroni's post-hoc test, $p>0.05$). Thus, it appeared that sera from autistic children could cause an increase in oxidative stress in primary cortical neurons which was counteracted by pretreatment with P6.

Levels of Neurotrophic Factors are Altered in Sera from Autistic Children

The inappropriate brain milieu because of altered levels of various neurotrophic factors in the sera has been hypothesized to play a major role in abnormal brain development in autistic individuals. The levels of various key neurotrophic factors were evaluated in the 3 pairs of autism/control sera (Table 2) which induced increased cell death and oxidative stress in primary cultured cortical neurons. Indeed, the levels of various neurotrophic factors were found to be altered in sera from autistic children compared to those from age and gender matched control children as evaluated by quantitative Western blots (FIG. 2). The levels of mature CNTF and BDNF were markedly decreased in autism sera (FIGS. 2A&B; CNTF, Student's t-test, $p=0.0026$; BDNF, Student's t-test, $p=0.027$). Conversely, the levels of pro-BDNF, FGF-2, and LIF were found to be increased in autism sera compared to control (FIGS. 2A&B; pro-BDNF, Student's t-test, $p=0.0043$; LIF, Student's t-test, $p=0.0216$; FGF-2, Student's t-test, $p=0.0194$). No statistically significant differences were observed in the levels of NGF (FIGS. 2A&B, Student's t-test, $p=0.5693$). These data suggested the presence of neurotrophic abnormalities in the sera from autistic children that could have contributed to altered development of neurons and increase in cell death and oxidative stress found above in FIG. 1.

Sera from autistic children induce developmental delay in rat pups which can be rescued by co-treatment with P6.

The Wistar rat pups were injected intracerebroventricularly with autism or control sera with or without P6 within 24 hours of birth to evaluate their possible neurotoxic effect and potential neuroprotection by P6 in vivo. The in vivo studies were carried out using the same 3 pairs of autism/control sera as above for in vitro studies. Five groups of animals of 5-6/group were employed (FIG. 3A): (1) sham group injected with saline; (2) pups injected with sera from autistic children (5-6 rat pups for each serum); (3) pups injected with sera from normal healthy controls (5-6 rat pups for each serum); (4) pups injected with sera from autistic children plus P6 (5-6 rat pups for each serum); and (5) pups injected with sera from controls plus P6 (5-6 rat pups for each serum). The body weight recorded daily for infant rats (both male and female) from postnatal day 1 to postnatal day 21 did not differ significantly among the groups, as seen in FIG. 7 (repeated measures 2-way ANOVA; group effect, $F=0.36$ (4, 672), $p=0.836$).

In neurobehavioral development study, autism serum injected pups displayed a significant delayed development of surface righting reflex compared to saline injected sham group and control serum group (FIG. 3B, panel 1; ANOVA, $p=0.0049$, sham vs. autism serum group, Bonferroni's post-hoc test, $p<0.01$, autism serum vs. control serum group, $p<0.05$). Autism serum with P6 injected group showed a trend towards earlier development of surface righting compared to autism serum alone group; however, the difference did not reach statistical significance (FIG. 3B, panel 1; autism serum vs. autism serum+P6, Bonferroni's post-hoc test, $p>0.05$, Student's t-test, $p=0.074$).

Similarly, autism serum injected pups showed delayed appearance of negative geotaxis as compared to sham and control serum pups (FIG. 3B, panel 1; ANOVA, $p=0.0018$, sham vs. autism group, Bonferroni's post-hoc test, $p<0.01$, autism serum vs. control serum group, $p<0.01$). Autism serum with P6 group showed earlier development of negative geotaxis reflex compared to autism serum group (FIG. 3B, panel 1; Bonferroni's post-hoc test, $p>0.05$, Student's t-test, $p=0.044$). Besides delay in appearance of negative geotaxis, autism serum group also took longer times to turn 180° to head up position and move towards the top of the metallic grid in negative geotaxis testing over the period of development, as seen in FIG. 8A (repeated measures 2-way ANOVA; group effect, $F=4.78$ (4, 219), $p=0.001$; postnatal day 8, sham vs. autism serum group, Bonferroni's post-hoc test, $p<0.05$; postnatal day 14, sham vs. autism serum group, Bonferroni's post-hoc test, $p<0.01$). Autism serum with P6 group showed a trend towards better performance compared to autism serum alone group, however, it was not statistically significant.

The appearance of cliff aversion reflex did not differ significantly across groups (FIG. 3B, panel 1; ANOVA, $p=0.8410$). The autism serum injected pups took longer time to show cliff aversion compared to sham group during the observed period of development; however, it was not statistically significant, as seen in FIG. 8B (repeated measures 2-way ANOVA, group effect, $F=1.68$ (4, 219), $p=0.1567$; sham vs. autism serum group, Bonferroni's post-hoc test, $p>0.05$), and P6 treatment had no detectable effect on cliff aversion reflex.

The tests for rooting reflex and forelimb grasp did not reveal any significant differences among groups (FIG. 3B1; rooting, ANOVA, $p=0.1044$; forelimb grasp, ANOVA, $p=0.2626$). Similarly, the appearance of eye opening and auditory startle did not differ between groups (FIG. 3B2, eye opening, ANOVA, $p=0.9708$; auditory startle, ANOVA, $p=0.3677$).

The development of air righting which like surface righting is a measure of labyrinthine reflex and motor coordination was significantly delayed in autism serum injected pups compared to sham group and control serum group; this developmental delay was significantly corrected by P6 treatment (FIG. B2; ANOVA, $p=0.0002$; sham vs. autism group, Bonferroni's post-hoc test, $p<0.01$; autism serum vs. control serum group, $p<0.001$; autism serum vs. autism serum+P6 group, Bonferroni's post-hoc test, $p<0.05$). Similarly, development of ear twitch reflex was markedly delayed in autism serum injected pups compared to sham and control serum groups but P6 had no significant effect (FIG. 3B2; ANOVA, $p<0.0001$; sham vs. autism group, Bonferroni's post-hoc test, $p<0.001$; autism serum vs. control serum group, $p<0.01$; autism serum vs. autism serum+P6 group, Bonferroni's post-hoc test, $p>0.05$).

Finally, fore limb placing was significantly delayed in autism serum injected animals compared to sham and control serum groups and the performance in autism serum with P6 group was improved (FIG. 3B2; ANOVA, $p=0.0075$; sham vs. autism group, Bonferroni's post-hoc test, $p>0.05$, Student's t-test, $p=0.0143$; autism serum vs. control serum group, $p<0.05$; autism serum vs. autism serum+P6 group, Bonferroni's post-hoc test, $p<0.05$).

Overall, the developmental milestones in rats which were affected by treatment with autism serum involved complex motor performance and skills; on the contrary, most of the neurodevelopmental behaviors which were unaltered in autism serum injected pups are known to be mediated by simplex reflex circuitry. P6 co-injected with autism serum was able to ameliorate the deficits in negative geotaxis, air righting and fore limb placement induced by autism serum.

Sera from Autistic Children Induce Deficits in Isolation-Induced Ultrasonic Vocalization Calls in Rat Pups Social communication deficit is one of the fundamental clinical phenotype of ASDs. Although rodents such as rats and mice do not use language, they emit auditory signals including USVs. USVs emitted by rat pups upon separation from the dam and littermates can be used to assess the ability of social communication. The number of isolation-induced ultrasonic calls was significantly lower in pups injected with sera from autistic children compared to saline injected sham group and control sera injected group on postnatal days 5, 7, and 9 [FIG. 4A; repeated measures 2-way ANOVA, group effect, $F=28.84$ (4, 365), $p<0.0001$; postnatal day 5, sham vs. autism serum group, Bonferroni's post-hoc test, $p<0.001$, autism serum vs control serum group, Bonferroni's post-hoc test, $p<0.001$; postnatal day 7, sham vs. autism serum group, Bonferroni's post-hoc test, $p<0.05$, autism serum vs control serum group, post-hoc test, $p<0.05$; postnatal day 9, sham vs. autism serum group, Bonferroni's post-hoc test, $p<0.01$, autism serum vs control serum group, post-hoc test, $p<0.01$]. No significant effect of P6 treatment was found on USVs emitted by the rat pups. The mean duration of ultrasonic calls did not differ between groups [FIG. 4B; repeated measures 2-way ANOVA, group effect, $F=1.79$ (4, 365), $p=0.1306$]. The decreased number of ultrasonic calls emitted after maternal and littermate isolation in rat pups injected with sera from autistic children suggest decreased propensity towards their mothers as is also common in autistic infants.

P6 Treatment can Rescue Social Approach and Novelty Impairments in Autism Sera Treated Young Rats During the first habituation phase of the 3-chamber social approach/novelty task, the grooming time as measured during the 5 min exploration of the central chamber did not differ between the different groups (FIG. 5A; ANOVA, $p=0.2988$). Nonetheless, there was a strong trend towards increased grooming time in young rats injected with sera from autistic children compared to the sham group suggesting an increased tendency towards a spontaneous repetitive behavior (FIG. 5A; Bonferroni's post hoc test, $p>0.05$; Student's t-test, $p=0.014$).

In the 3-chambered social arena test, young rats injected with sera from autistic children displayed dysfunctional social interaction behavior (one of the most recognizable manifestations of autistic behavior) compared to sham and control serum injected groups (FIG. 5B&C). The young rats injected with autistic sera spent much less time interacting with social partner (stranger 1) compared to sham and control serum groups; P6 treatment had no effect on this autistic behavior (FIG. 5B; sham vs. autism serum group, Bonferroni's post-hoc test, $p<0.001$, autism serum vs control serum group, Bonferroni's post-hoc test, $p<0.001$; autism serum vs autism serum+P6, Bonferroni's post-hoc test, $p>0.05$). Similar trends were observed for time spent in social partner chamber and empty cup chamber (FIG. 5C; sham vs. autism serum group, Bonferroni's post-hoc test, $p<0.001$, autism serum vs control serum group, Bonferroni's post-hoc test, $p<0.001$; autism serum vs autism serum+P6, Bonferroni's post-hoc test, $p>0.05$).

In a subsequent trial, when a novel social partner (stranger 2) was introduced, autism sera injected rats displayed a marked lack of preference for social novelty compared to sham and control serum groups; P6 treatment was able to rescue this deficit (FIG. 5C; sniffing time, sham vs. autism serum group, Bonferroni's post-hoc test, $p<0.001$, autism serum vs control serum group, Bonferroni's post-hoc test, $p<0.001$; autism serum vs autism serum+P6, Bonferroni's post-hoc test, $p<0.001$; time spent in stranger 2 chamber, sham vs. autism serum group.

Bonferroni's post-hoc test, $p<0.001$, autism serum vs control serum group, Bonferroni's post-hoc test, $p<0.05$; autism serum vs autism serum+P6, Bonferroni's post-hoc test, $p<0.05$). These data suggest that the dysfunction in social novelty which is also a measure of short-term social memory induced by sera from children with autism was rescued by P6.

The autism sera did not induce any significant changes in the level of anxiety, exploratory activity, motor performance, or depression in rats, as seen in FIG. 9.

Sera from Autistic Children Induce Neurodegeneration and Increase Oxidative Stress in Young Rats Brains which is Counteracted by P6 Probably Via Increase in BDNF Expression In parallel with the in-vitro studies utilizing primary cultured cortical neurons, the in vivo effect of sera from autistic and control children and potential neuroprotective effect of P6 on neurodegeneration and oxidative stress was investigated in the cerebral cortex of young rats. Fluorojade C histochemical staining, a sensitive marker of neurodegeneration, confirmed a marked increase in neurodegeneration in autism serum injected rats compared to sham and control serum group; P6 was able to significantly reduce this autism serum induced neurodegeneration (FIGS. 6A&B; ANOVA, $p<0.0001$; sham vs. autism group, Bonferroni's post-hoc test, $p<0.001$; autism serum vs. control serum group, Bonferroni's post-hoc test, $p<0.01$; autism serum vs. autism serum+P6 group, Bonferroni's post-hoc test, $p<0.05$). Similarly, a marked increase in 8-OHdG positive neurons, a marker of DNA damage caused by oxidative free radicals, was observed in autism serum injected rats; P6 also exerted a beneficial effect here (FIGS. 6C&D; ANOVA, $p<0.0001$; sham vs. autism group, Bonferroni's post-hoc test, $p<0.001$; autism serum vs. control serum group, Bonferroni's post-hoc test, $p<0.001$; autism serum vs. autism serum+P6 group, Bonferroni's post-hoc test, $p<0.05$). Collectively, these data provided the anatomical and physiological basis for the behavioral abnormalities observed in autism sera injected rats and the potential therapeutic beneficial effect of P6.

The effect of sera with or without P6 treatment on the expression of BDNF and CNTF in rat brain tissue was also investigated. The densitometric quantification of Western blots developed with anti-BDNF and normalized to GAPDH revealed decreased levels of both pro-BDNF and mature BDNF in autistic sera treated rat brains compared to control sera treatment (FIGS. 6E&F; Bonferroni's post-hoc test, $p<0.05$ for both pro-BDNF and BDNF). P6 (20 nM) co-treatment was able to correct the autistic sera induced reduction in both pro-BDNF and BDNF expression (FIGS. 6E&F; pro-BDNF, Bonferroni's post-hoc test, $p<0.001$; BDNF, Bonferroni's post-hoc test, $p<0.01$). These data suggests that the beneficial effect of P6 on behavioral abnormalities in autism sera treated rats could be because of rescue of BDNF level.

The CNTF levels did not differ significantly between sham, autism serum, autism serum+P6, and control serum groups (FIGS. 6E&F; Bonferroni's post-hoc test, $p>0.05$); however, there was a significant increase in CNTF expression in control serum+P6 group compared to control serum alone group (FIGS. 6E&F; Bonferroni's post-hoc test, $p>0.05$; Student's t-test, $p=0.0155$).

The present example shows that alterations in the levels of neurotrophic factors in the sera from autistic individuals could contribute to neurobehavioral phenotype of autism in rats. In particular, a CNTF small peptide mimetic, P6, can rescue the ASD specific deficits in rats, probably by inducing an increase in BDNF level. This example provides a basis for neurotrophic factors based serum/plasma screening assay for autism and a potential therapeutic strategy via modulation of neurotrophic support. Furthermore, the intracerebroventricular treatment of newborn rats with sera from children with autism provides a potential useful animal model of the disease.

The present example suggests that dysfunction of brain environment in autism can contribute to behavioral deficits. Exposing the cultured neurons and early postnatal brains to sera from autistic children resulted in neurodegeneration, increased oxidative stress, and behavioral impairments. It has been hypothesized that the abnormal behavioral phenotype of autism may result from structural and functional alterations in brain caused by abnormalities in brain development during embryonic period and early postnatal life. Increased oxidative stress and imbalance of neurotrophic factors could be major contributing factors to pathophysiology of autism. During early brain development, neurotrophic factors provide an appropriate brain milieu necessary for all aspects of neural development including neuronal proliferation, differentiation, growth, and migration. Similarly, neurogenesis is highly sensitive to oxidative stress induced damage; hippocampal neurogenesis is reported to be reduced after exposure to oxidative stress in vivo in an environment lacking antioxidant enzymes. Thus, impaired neurotrophic balance and increased oxidative stress could alter the early brain development and lead to an autistic behavioral phenotype.

The beneficial effect observed with P6 treatment further strengthens the idea that autism could be caused by an early imbalance of neurotrophic factors and increased oxidative stress. P6 pretreatment prevented cell death induced by autism sera in primary cultured cortical neurons. In the current study, P6 was able to rescue autism serum-induced neurodegeneration and oxidative stress in cultured neurons and rat brains. The neuroprotective effect of P6 against autism serum-induced neurodegeneration and oxidative stress could be mediated via BDNF because of increased BDNF expression that was observed in P6 treated rat brains. Remarkably, P6 treatment was able to rescue these structural abnormalities, possibly via increased BDNF expression.

This example provides evidence regarding the neurotrophic abnormalities in autism and the potential role they play in the pathophysiology of the disease. The brain milieu of autistic children is altered and favors increased oxidative stress and neurodegeneration. Ameliorating the neurotrophic imbalance during early stages of brain development can serve as a potential therapeutic approach for autism. Based on the example, P6 represents a new class of neurotrophic peptide mimetics that has potential therapeutic value for ASD and related conditions.

The compound of the present invention may be administered as such or after its modification, such as the addition of an adamantylated amino acid (e.g., adamantylated glycine or glutamate) at its C-terminus or N-terminus (or both) to increase its stability or to generate a cyclized form of the peptide or its mirror image in D-form amino acids. The compound can be administered in liquid form or as a slow release tablet or capsule orally, or in liquid form intravenously, subcutaneously or as a patch or as a nasal inhaler. The treatment may be started as early as prenatally or early postnatally and be performed preventatively. For example, the compound could be administered prenatally through the mother of the fetus (placentally), starting with the second trimester, and/or early postnatally through oral routes such as through the milk of the mother or combined with infant formula. The amount of the compound sufficient to produce beneficial effect is an appropriate amount that achieves nanomolar concentration levels in sera and thus picomolar levels in the brain.

SEQUENCE LISTING

```
<160> NUMBER OF SEQ ID NOS: 1

<210> SEQ ID NO 1
<211> LENGTH: 11
<212> TYPE: PRT
<213> ORGANISM: Artificial Sequence
<220> FEATURE:
<223> OTHER INFORMATION: human ciliary neurotrophic factor mimetic

<400> SEQUENCE: 1

Val Gly Asp Gly Gly Leu Phe Glu Lys Lys Leu
1               5                   10
```

One of the most remarkable results of the example is the development of several features of autism in young rats whose brains were exposed to sera from autistic children via i.c.v. injections. This result strongly suggests the important role brain environment plays during early development in the pathophysiology of autism. Early postnatal exposure of brain tissue to sera from autistic children which had abnormalities in neurotrophic factor levels led to developmental delay and social communication, interaction, and memory deficits in young rats. Several of these deficits, such as developmental delay and social memory deficits, were rescued by P6 treatment. Interestingly, the early postnatal exposure to autistic sera resulted in increased oxidative stress induced DNA damage and neurodegeneration in cortical tissue of young rats, providing the structural correlate for the behavioral abnormalities observed in these rats.

What is claimed is:

1. A method of treating a subject having an autism spectrum disorder, comprising the step of administering a therapeutic amount of a peptide consisting of the amino acid sequence of SEQ ID NO: 1 to the subject.

2. The method of claim 1, wherein the C-terminus or the N-terminus amino acids of the peptide are adamantylated.

3. The method of claim 2, wherein the therapeutic amount of the peptide is sufficient to achieve picomolar concentrations in the brain of the subject.

4. The method of claim 1, wherein the peptide is administered to the subject prenatally.

5. The method of claim 1, wherein the peptide is administered to the subject postnatally.

6. The method of claim 1, wherein the peptide is administered to the subject postnatally via oral ingestion.

* * * * *